(12) United States Patent
Mayeaux

(10) Patent No.: US 7,225,690 B1
(45) Date of Patent: Jun. 5, 2007

(54) MULTI-CAVITY SAMPLE CYLINDER WITH INTEGRATED VALVING

(75) Inventor: Donald P. Mayeaux, St. Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 307 days.

(21) Appl. No.: 10/631,501

(22) Filed: Jul. 31, 2003

Related U.S. Application Data

(60) Provisional application No. 60/400,736, filed on Aug. 2, 2002.

(51) Int. Cl.
*G01N 1/22* (2006.01)
(52) U.S. Cl. .................................. 73/864.62
(58) Field of Classification Search ..............
73/864.62–864.63, 863.52, 863.57, 864.51, 73/864.91, 863.71
See application file for complete search history.

(56) References Cited

U.S. PATENT DOCUMENTS

| | | | | |
|---|---|---|---|---|
| 2,726,548 A | * | 12/1955 | Van Der List | 73/864.62 X |
| 3,085,439 A | * | 4/1963 | Price | 73/864.62 |
| 3,238,783 A | * | 3/1966 | Wright | 73/864.62 X |
| 3,253,469 A | * | 5/1966 | Norman | 73/864.62 X |
| 3,593,533 A | * | 7/1971 | Washington | 73/864.62 X |
| 3,635,092 A | * | 1/1972 | Maughan et al. | 73/864.62 |
| 4,008,621 A | * | 2/1977 | Ostojic et al. | 73/864.62 X |
| 4,487,055 A | * | 12/1984 | Wolf | 73/864.62 X |
| 4,882,939 A | * | 11/1989 | Welker | 73/864.63 |
| 5,096,093 A | * | 3/1992 | Wells | 73/864.62 X |
| 5,303,599 A | * | 4/1994 | Welker | 73/863.84 |
| 5,535,635 A | * | 7/1996 | Shaw | 73/864.62 X |
| 5,898,113 A | * | 4/1999 | Vecere | 73/864.62 |

FOREIGN PATENT DOCUMENTS

GB 2188437 A * 9/1987

* cited by examiner

*Primary Examiner*—Thomas P. Noland
(74) *Attorney, Agent, or Firm*—Joseph T. Regard, Ltd plc

(57) ABSTRACT

A system for obtaining a representative sample of a natural gas stream, particularly a stream which is at or below its hydrocarbon dew point temperature (H.C.D.P.). The preferred embodiment of the present invention contemplates a sample cylinder having a flexible isolation barrier and integrated valving to provide a controlled ingress of sample gas at nominal pressure differential. The system thereby avoids throttling of the sample gas and the inherent cooling problems associated therewith when the stream is at or below hydrocarbon dew point temperature. The flexible isolation barrier of the present invention is relatively inexpensive and is configured for quick and easy replacement, which may be routinely performed to insure sample integrity. Alternative embodiments of the invention contemplate a spherical sample cylinder configuration with flexible isolation barrier, as well as an improvement for piston-type sample cylinders to provide constant sample pressure.

25 Claims, 23 Drawing Sheets

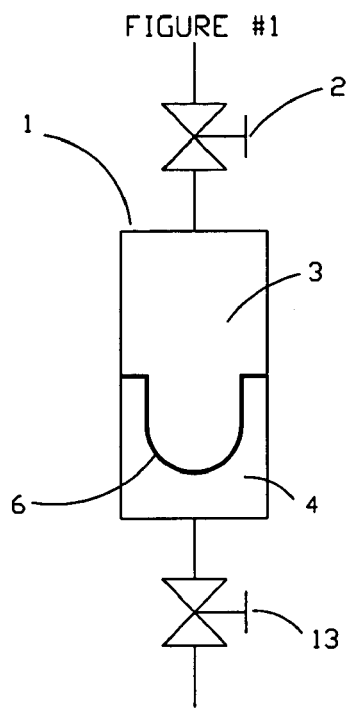
FIGURE #1
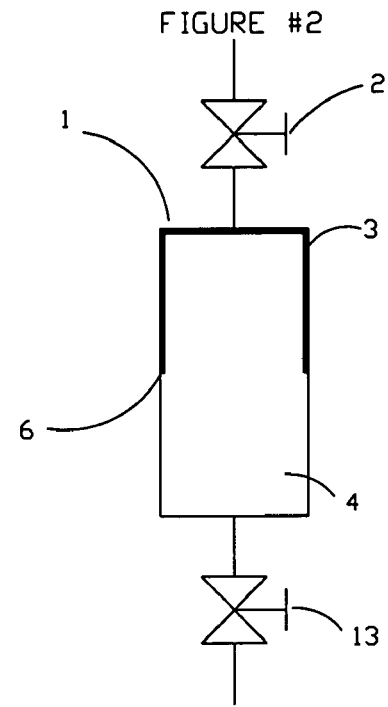
FIGURE #2
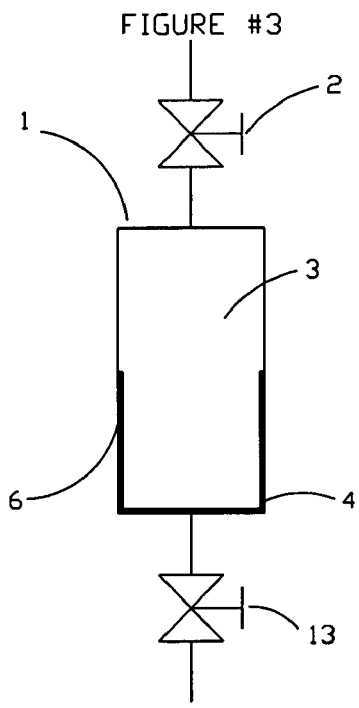
FIGURE #3
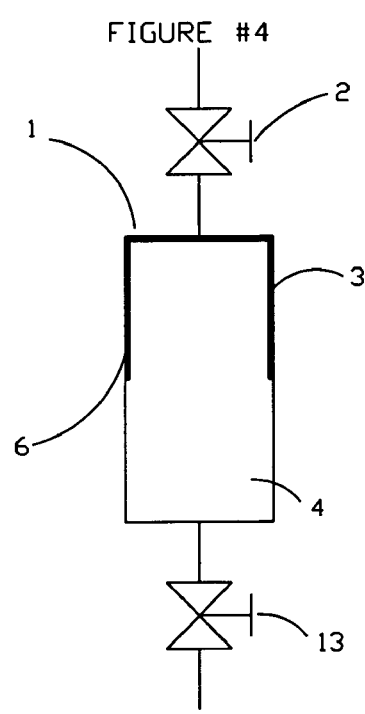
FIGURE #4

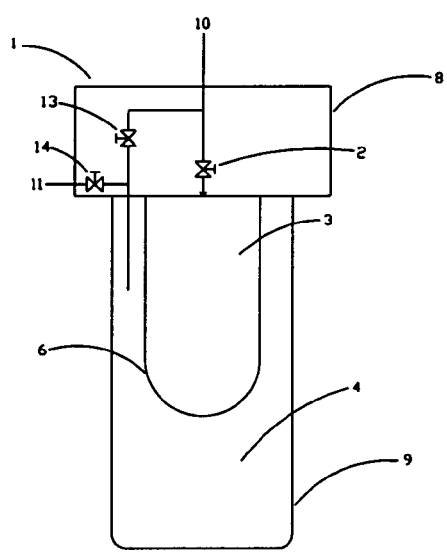
FIGURE #5
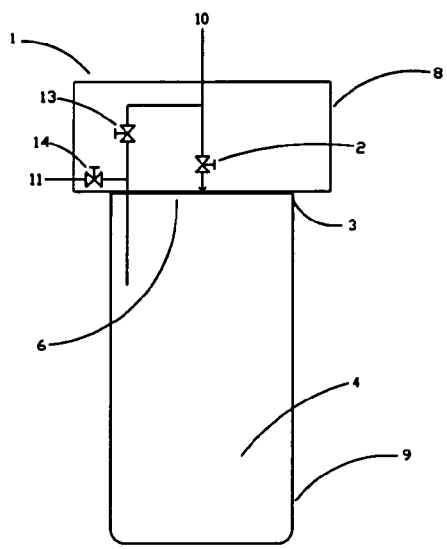
FIGURE #6
FIB conforms to CAVITY A
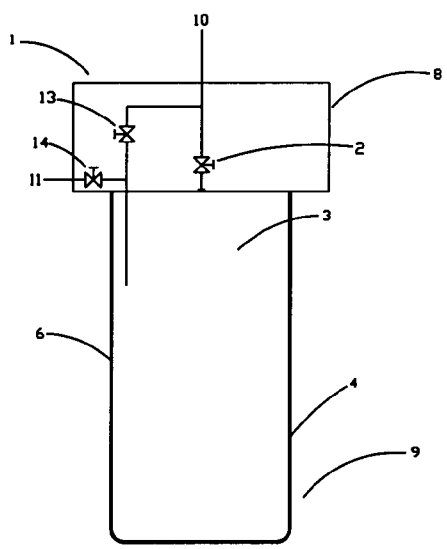
FIGURE #7
FIB conforms to CAVITY B
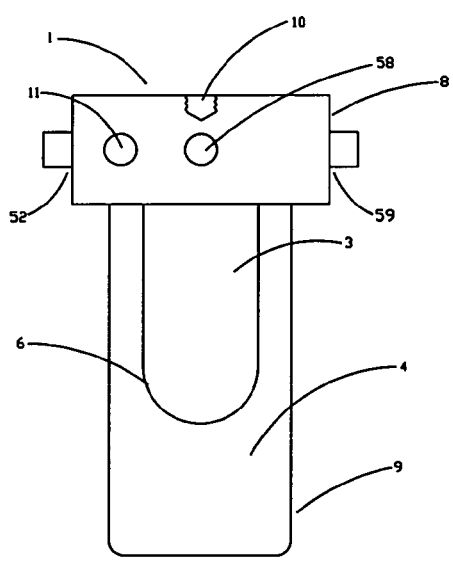
FIGURE #8

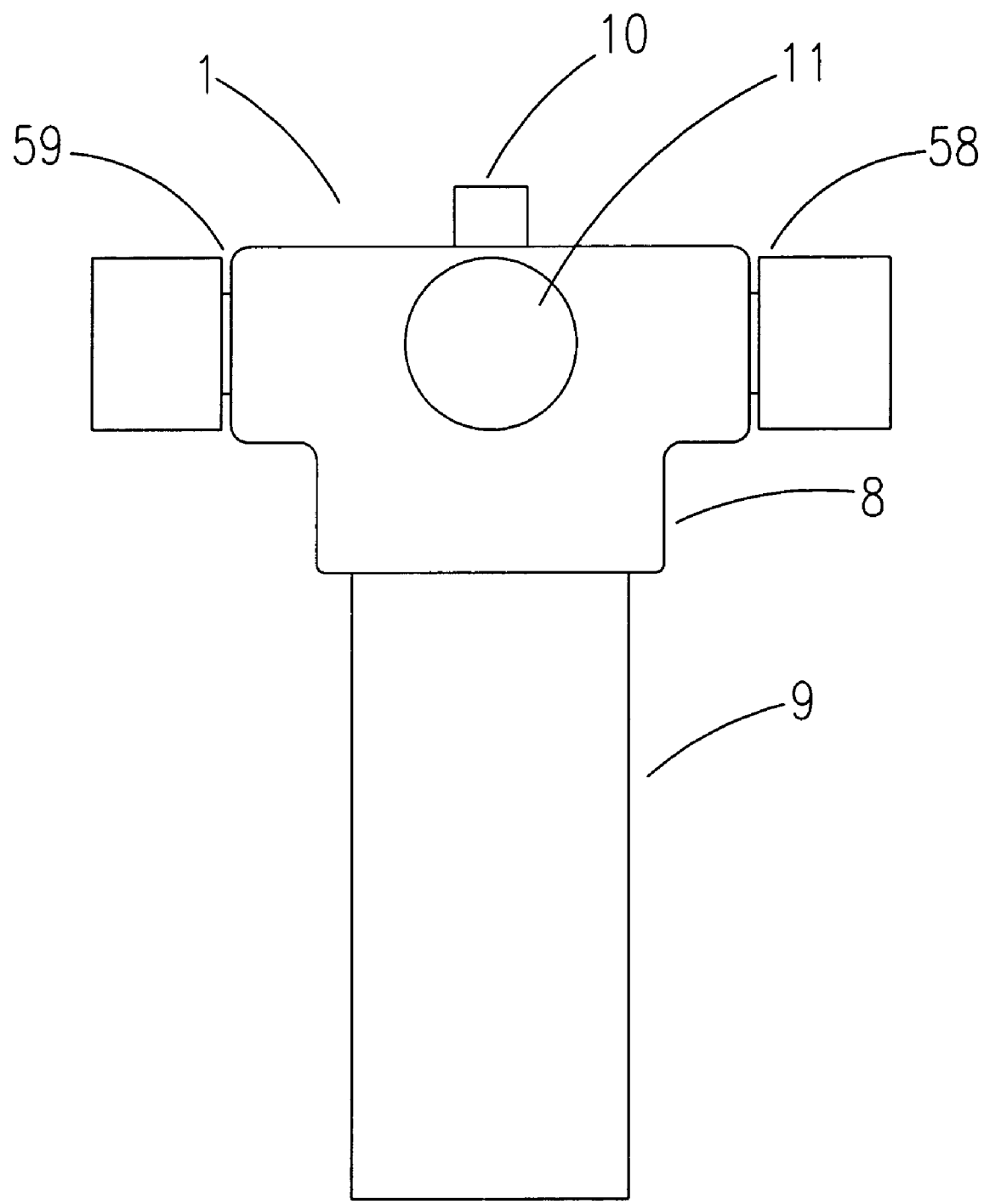
Figure #9

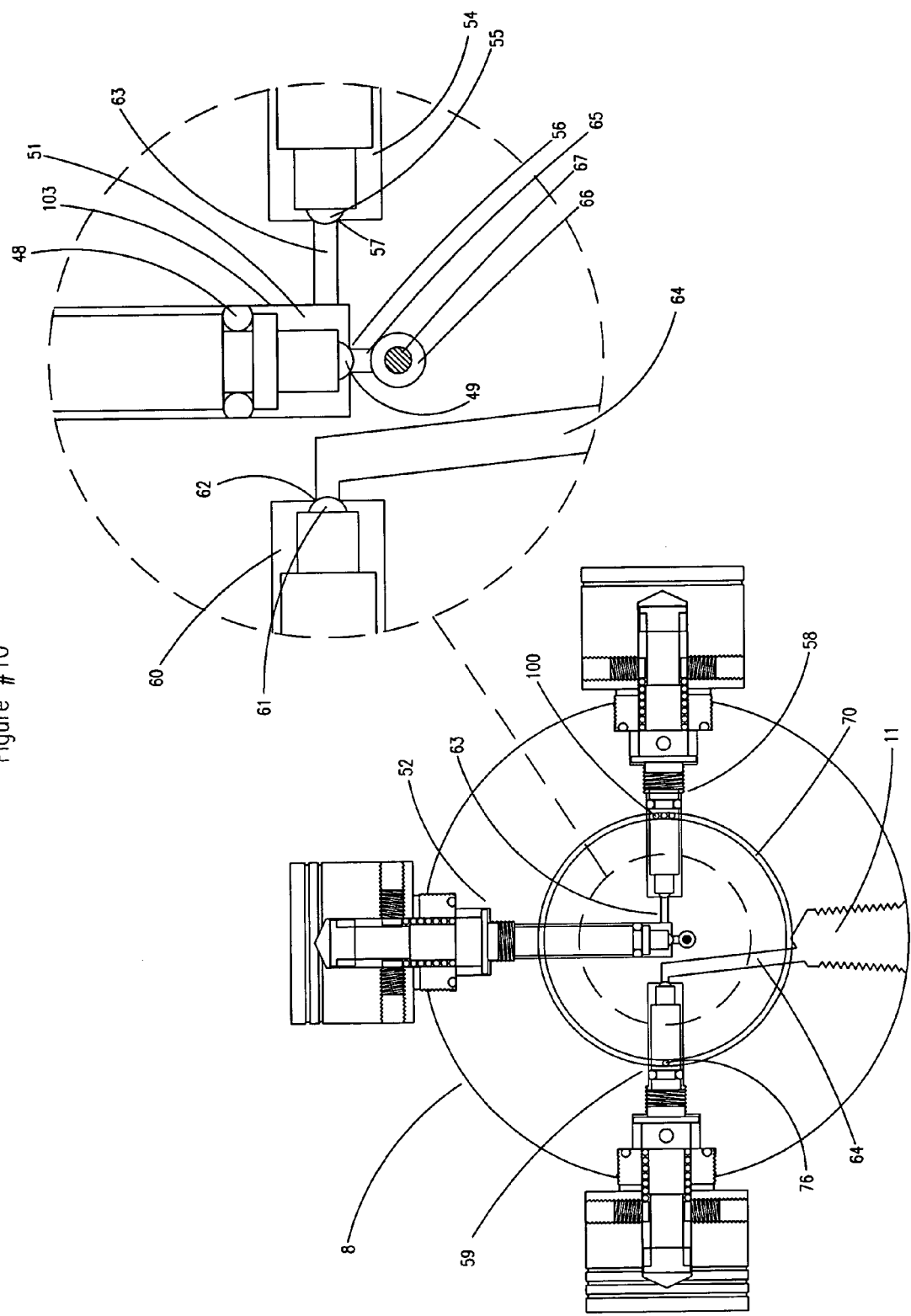
Figure #10

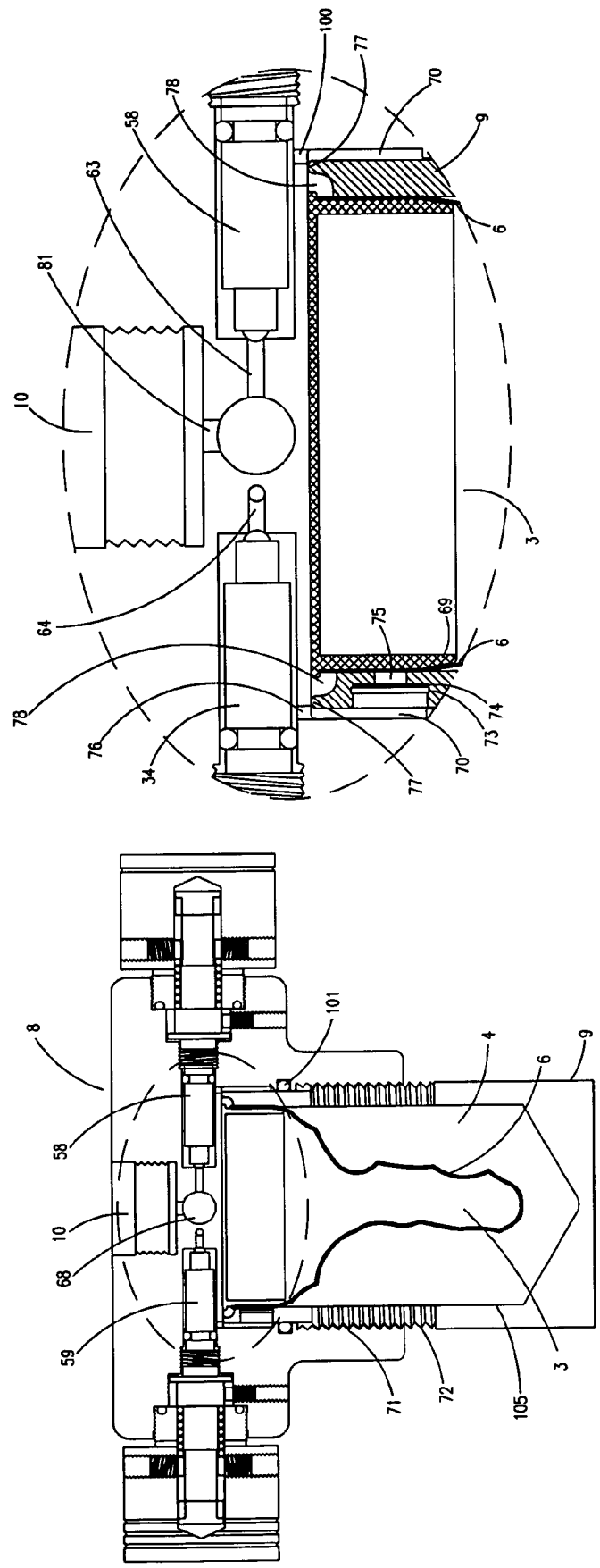
Figure #11

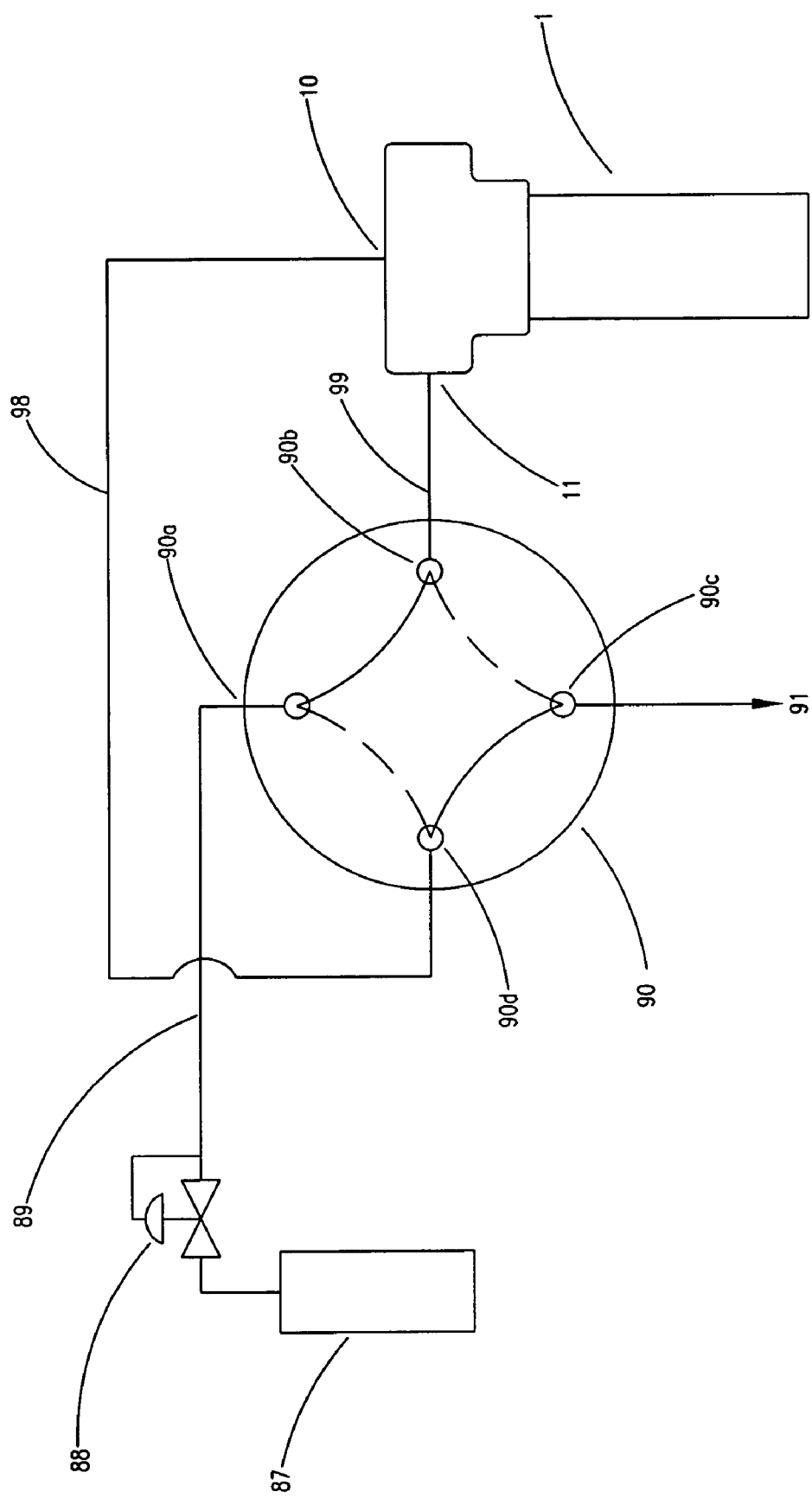
Figure #12

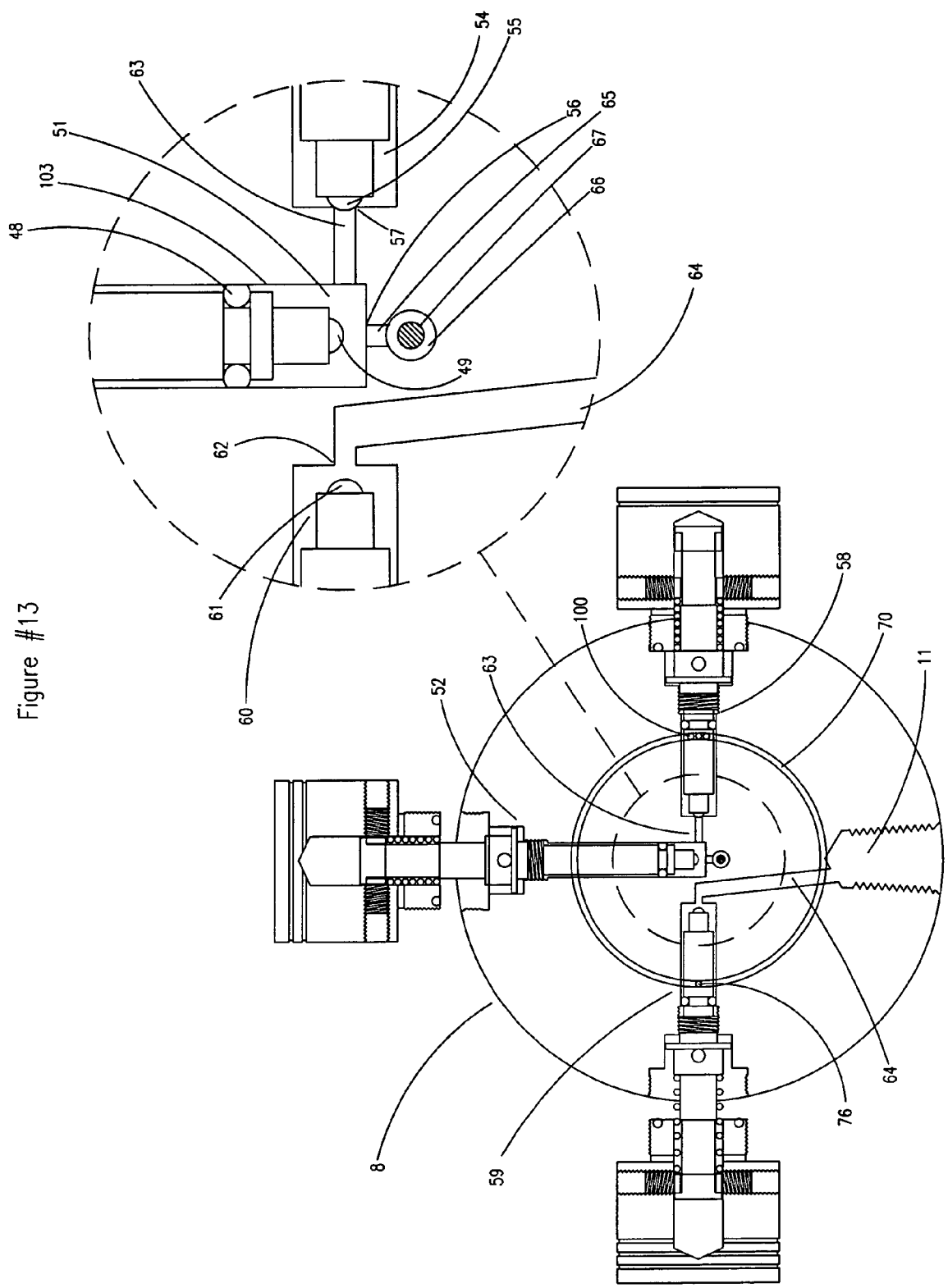
Figure #13

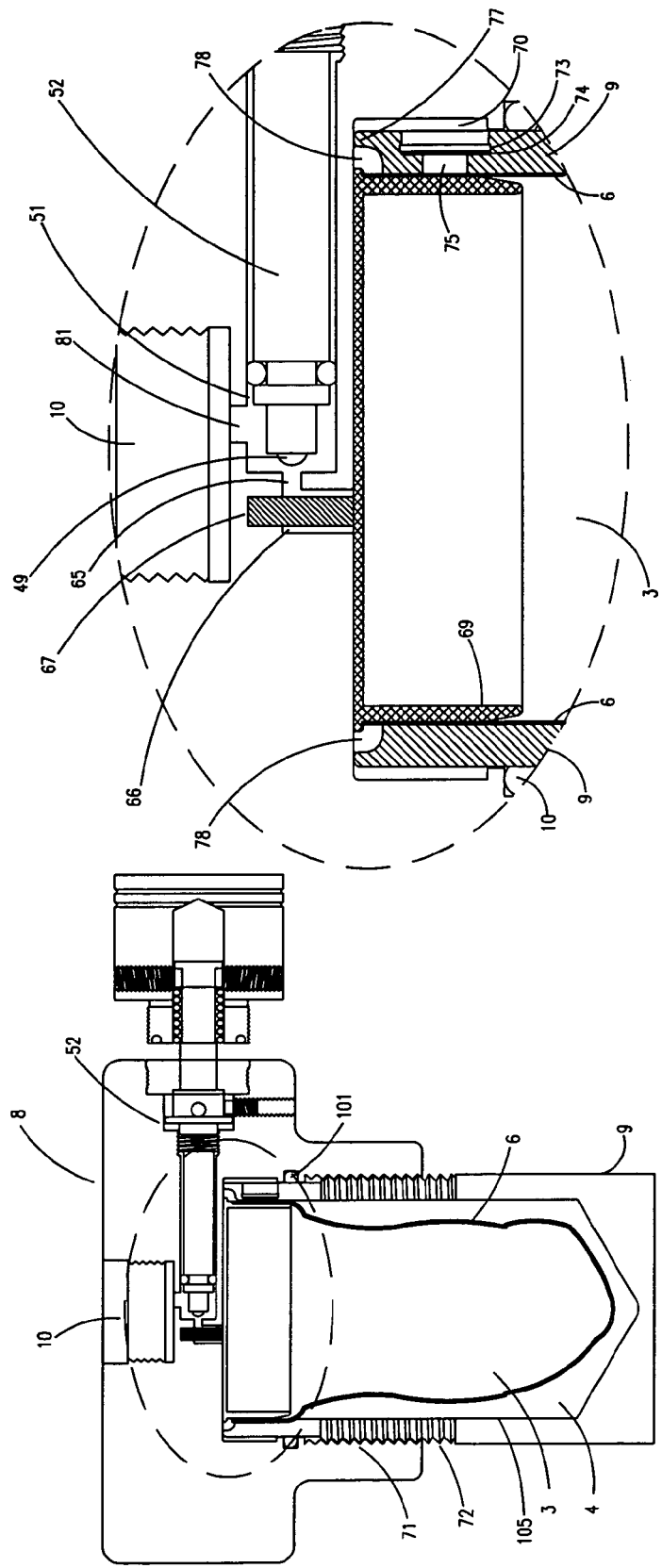
Figure #14

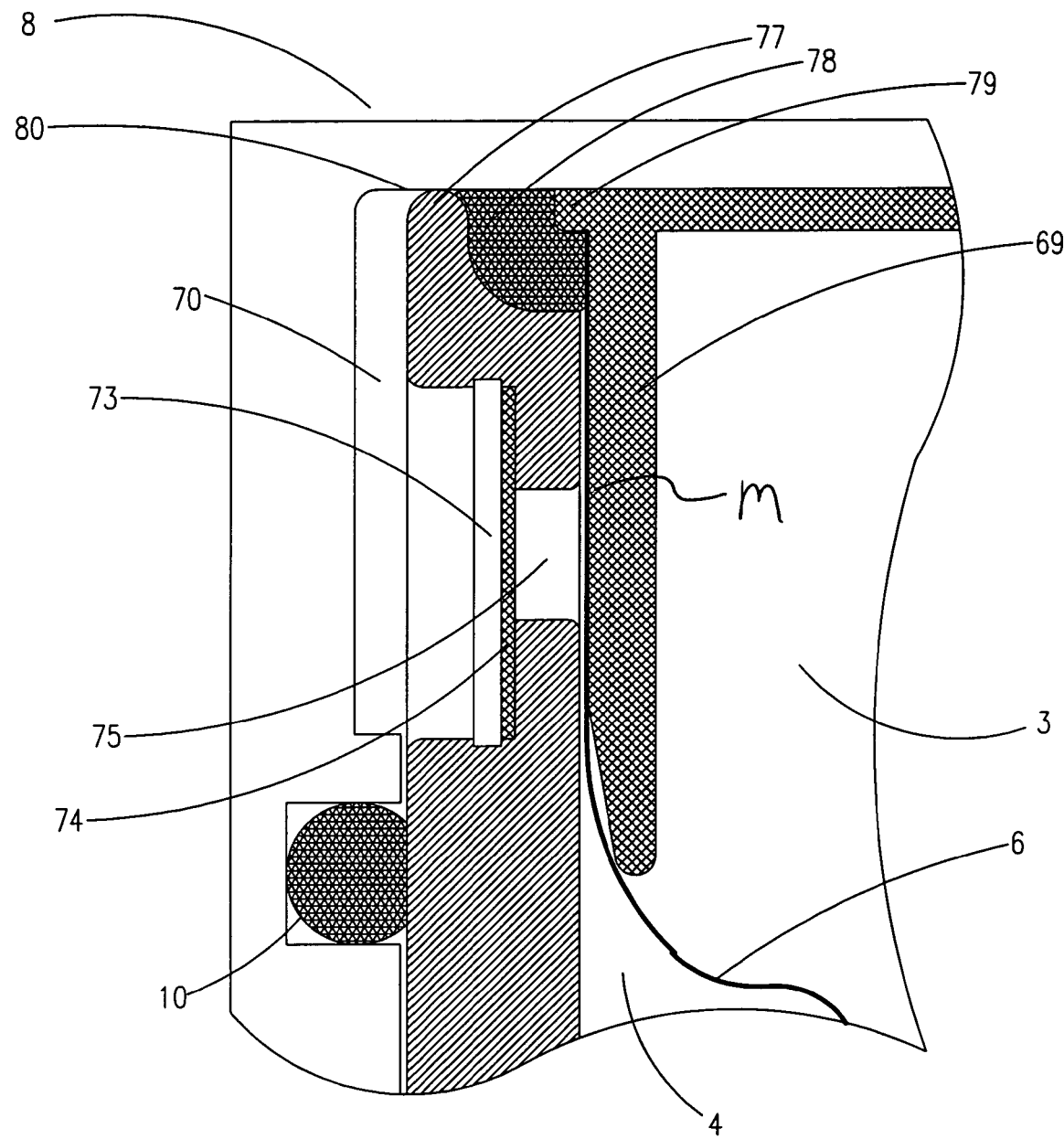
Figure #15

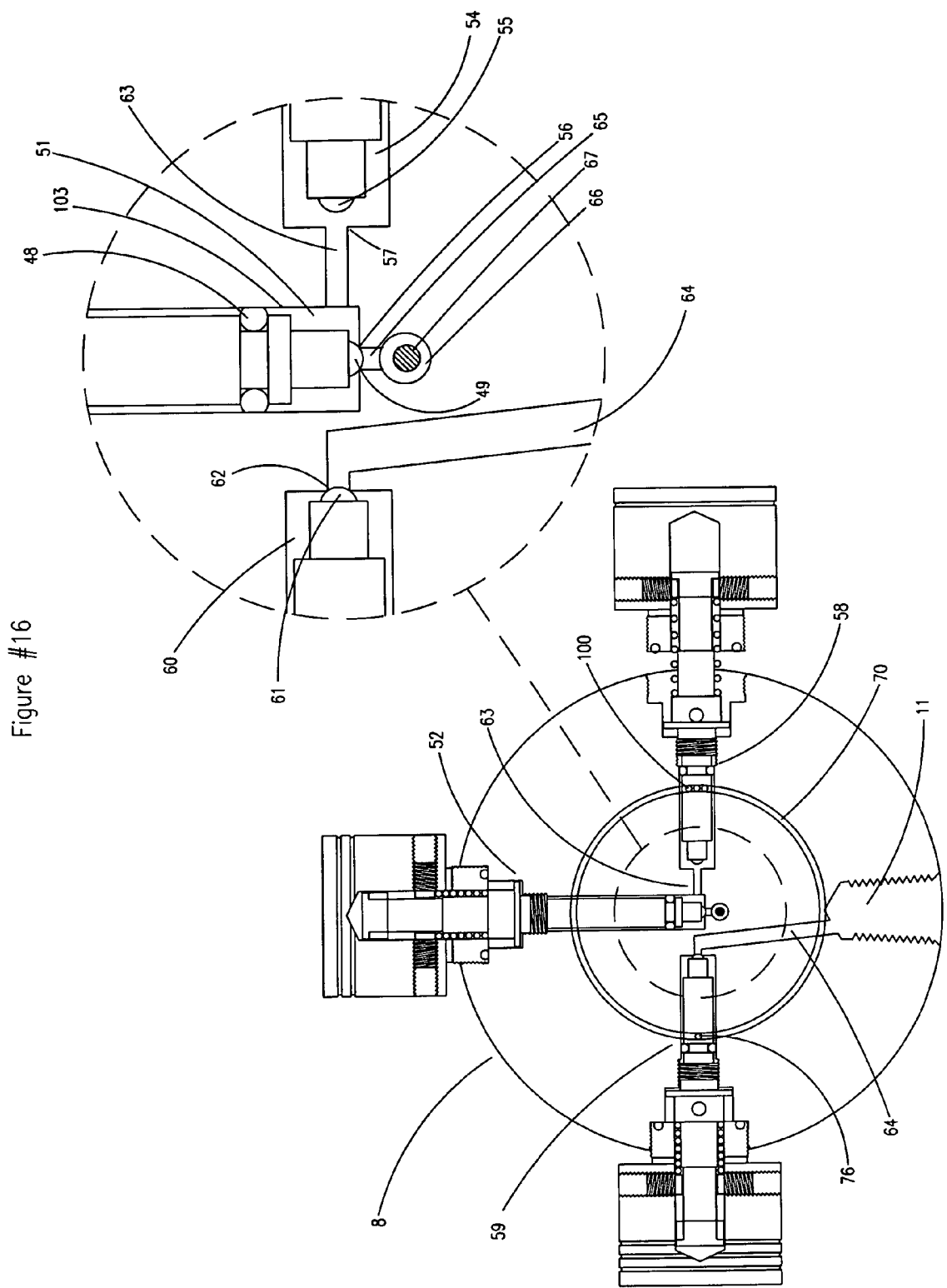
Figure #16

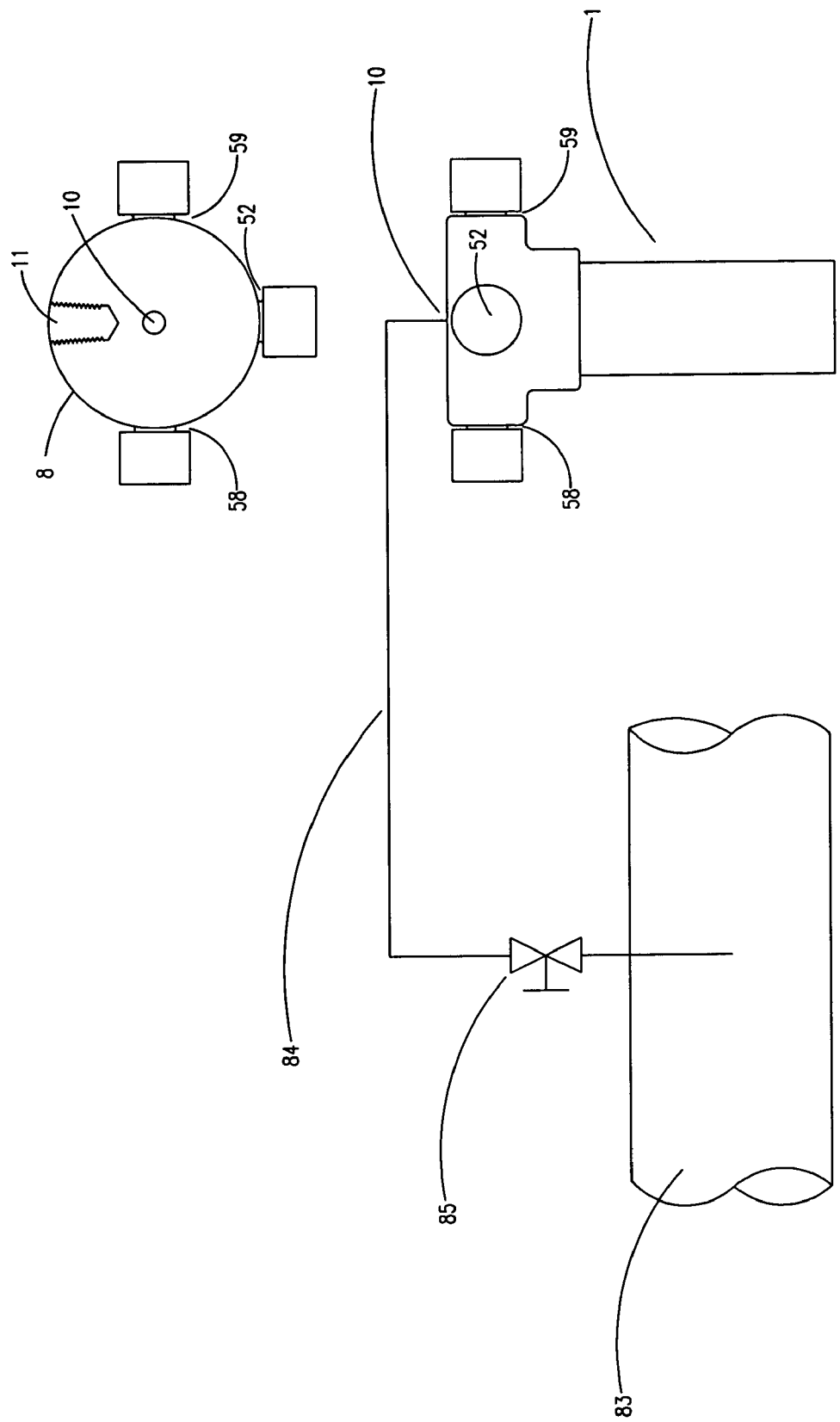
Figure #17

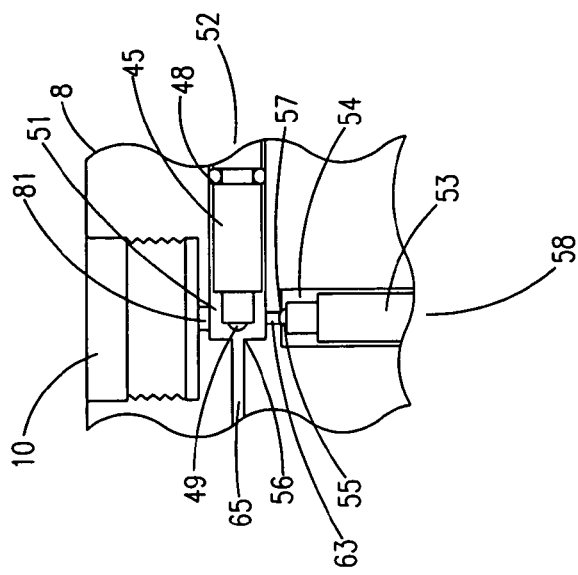
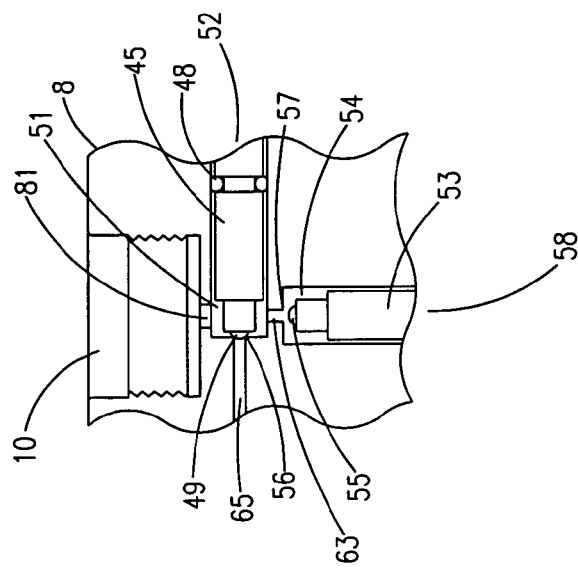
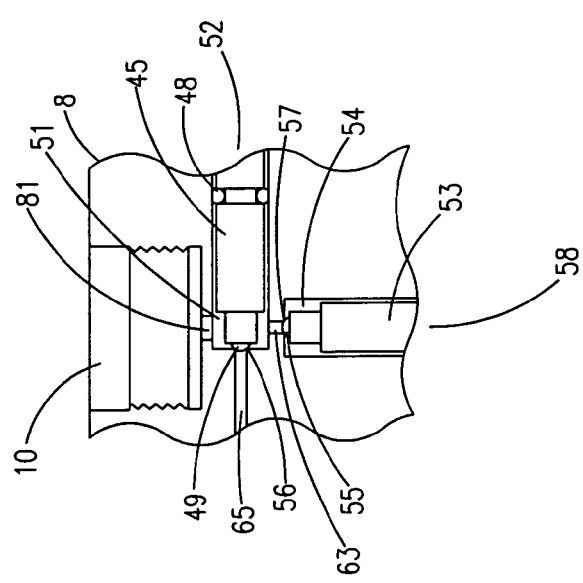

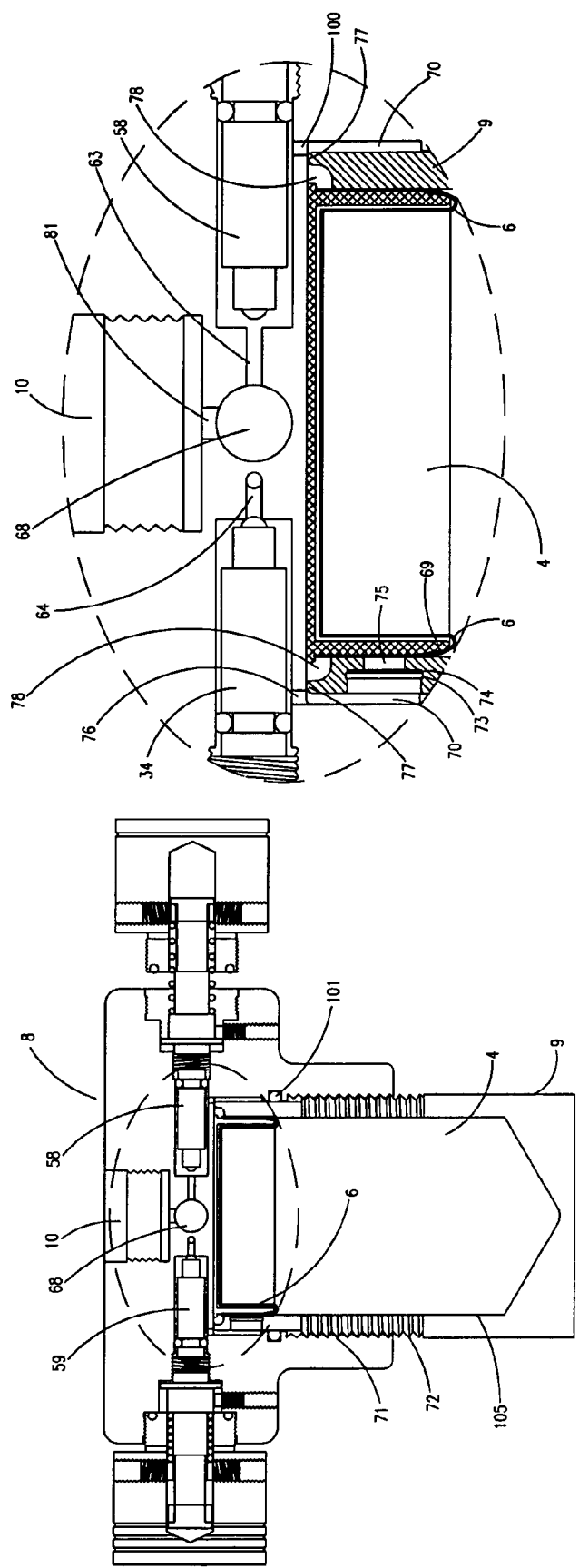
Figure #19

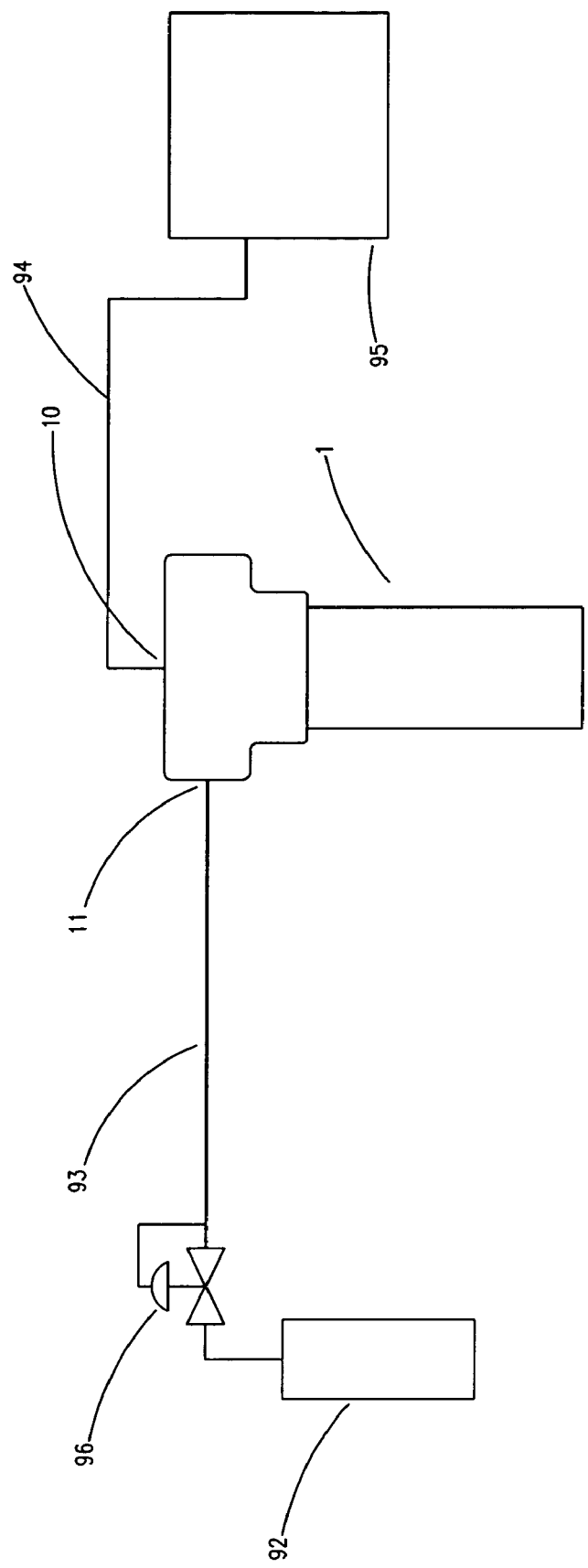
Figure #20

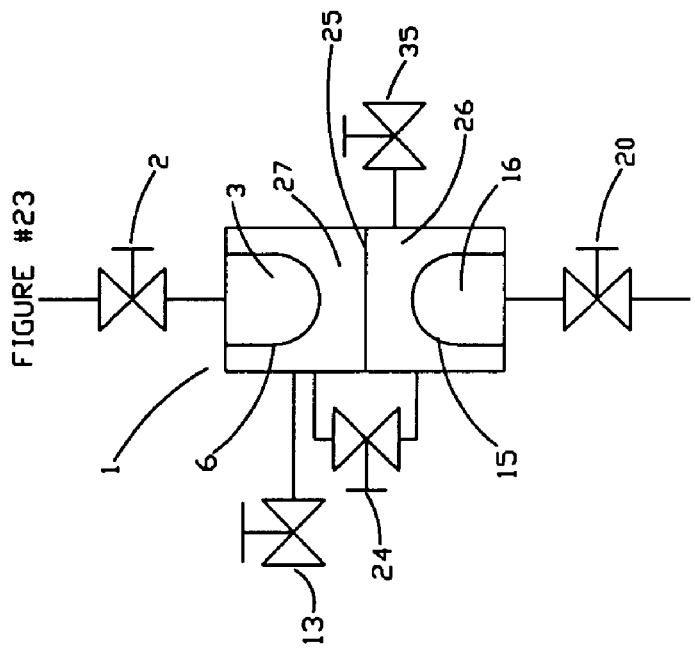
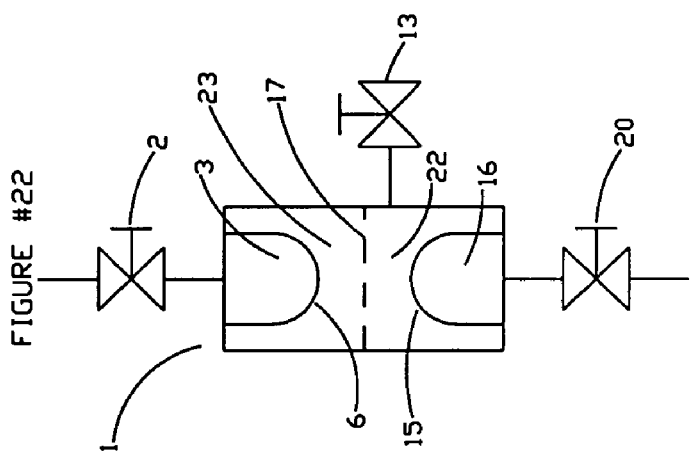
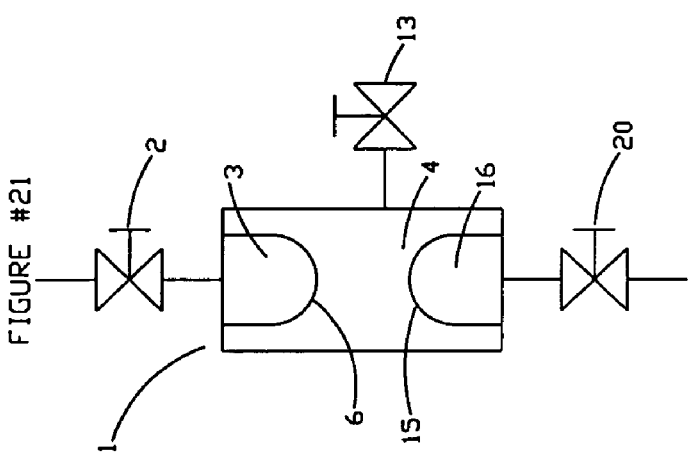

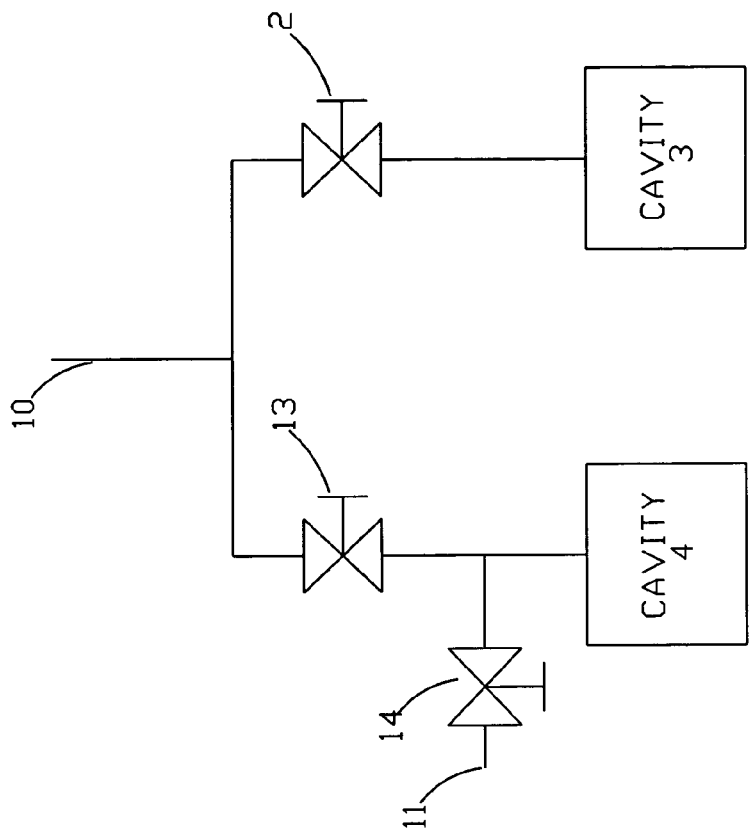
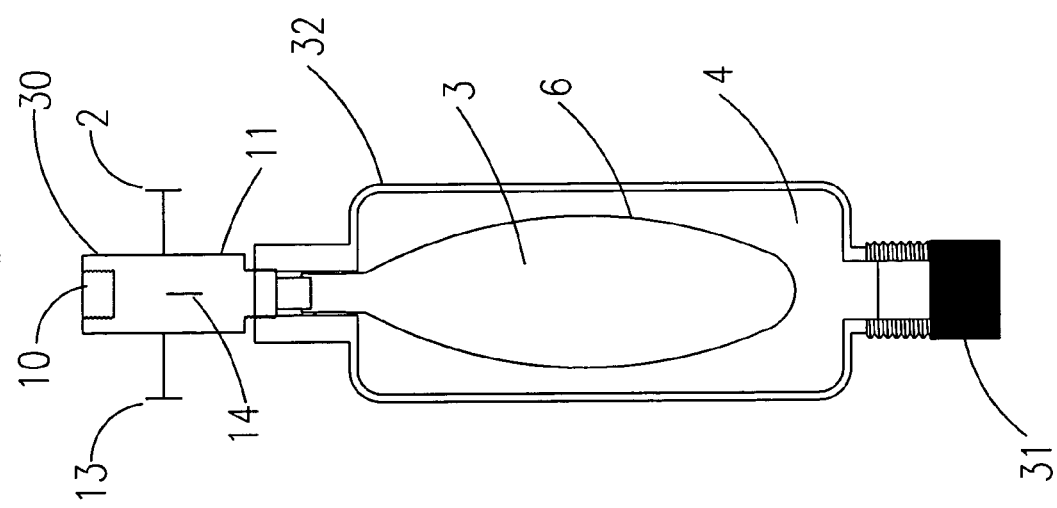

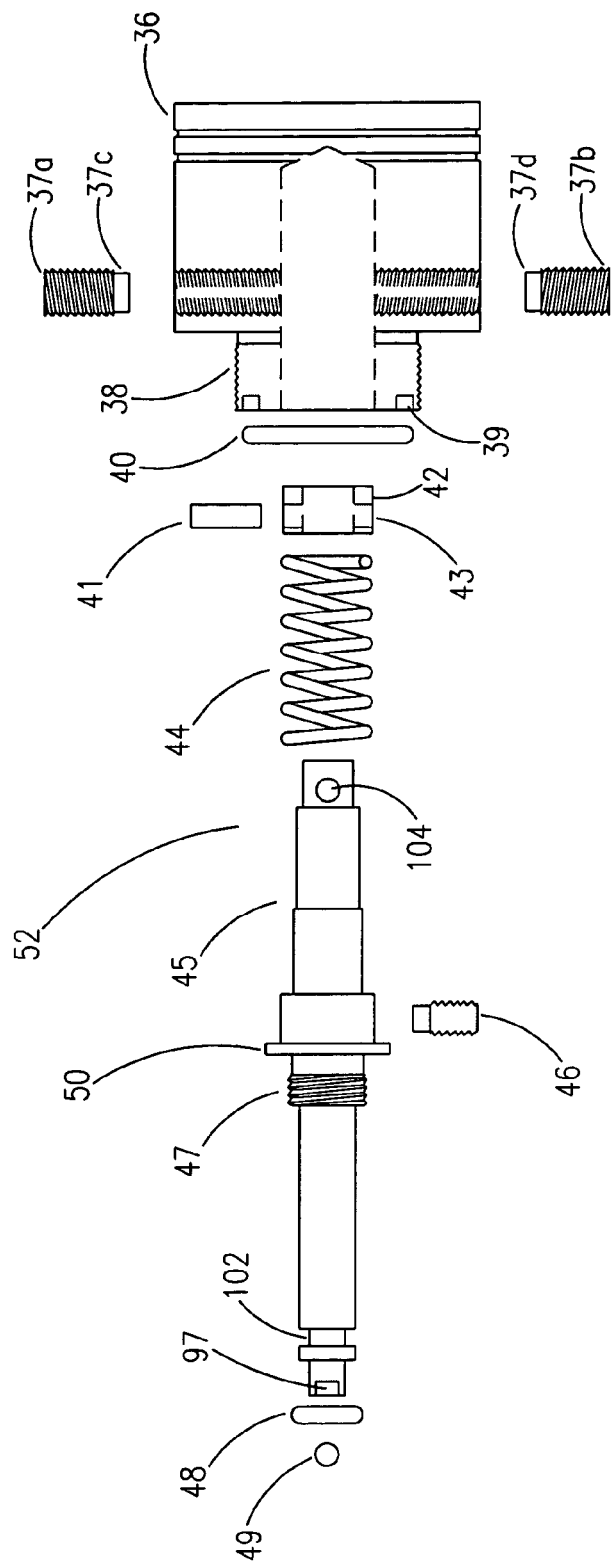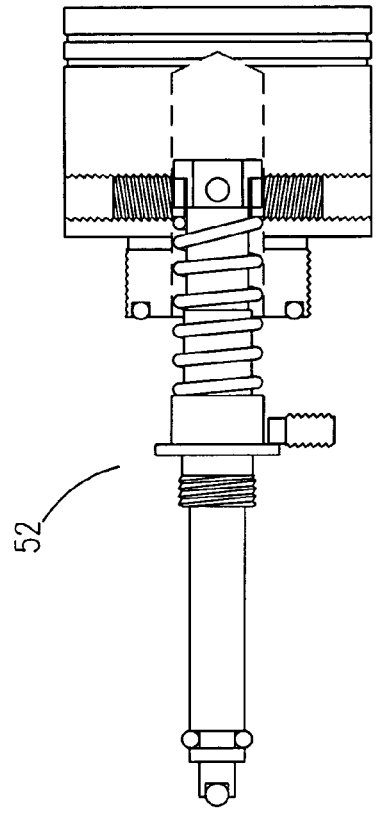
Figure #26a
Figure #26b

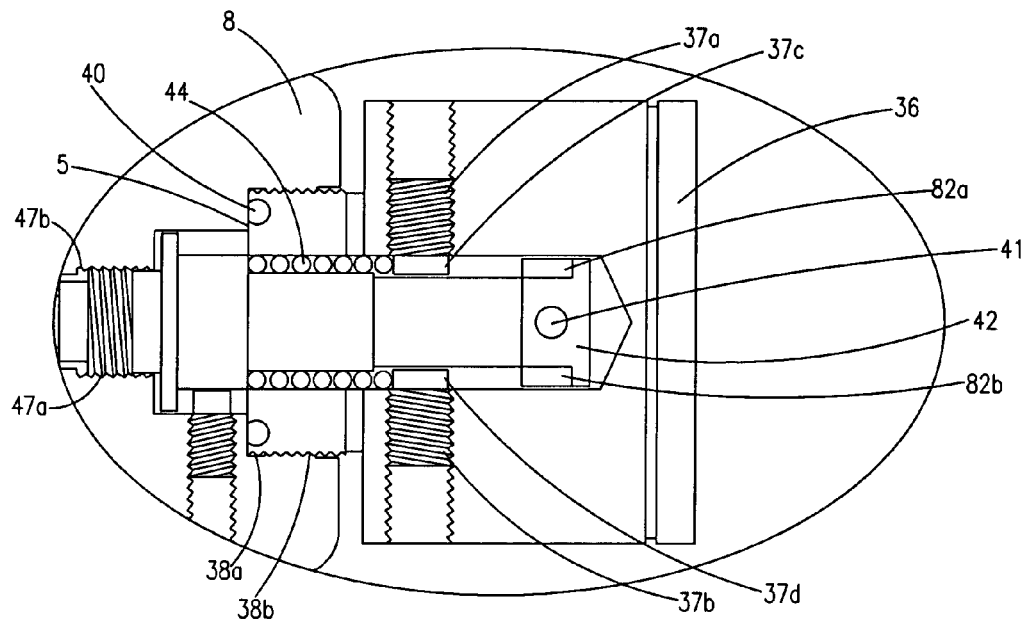
Figure #28a
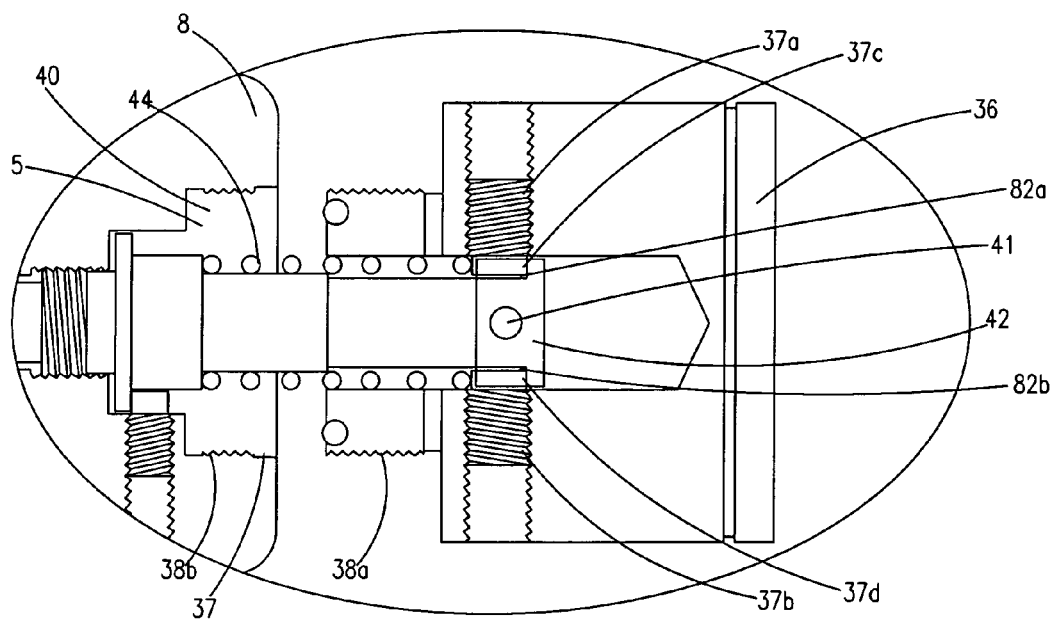
Figure #28b

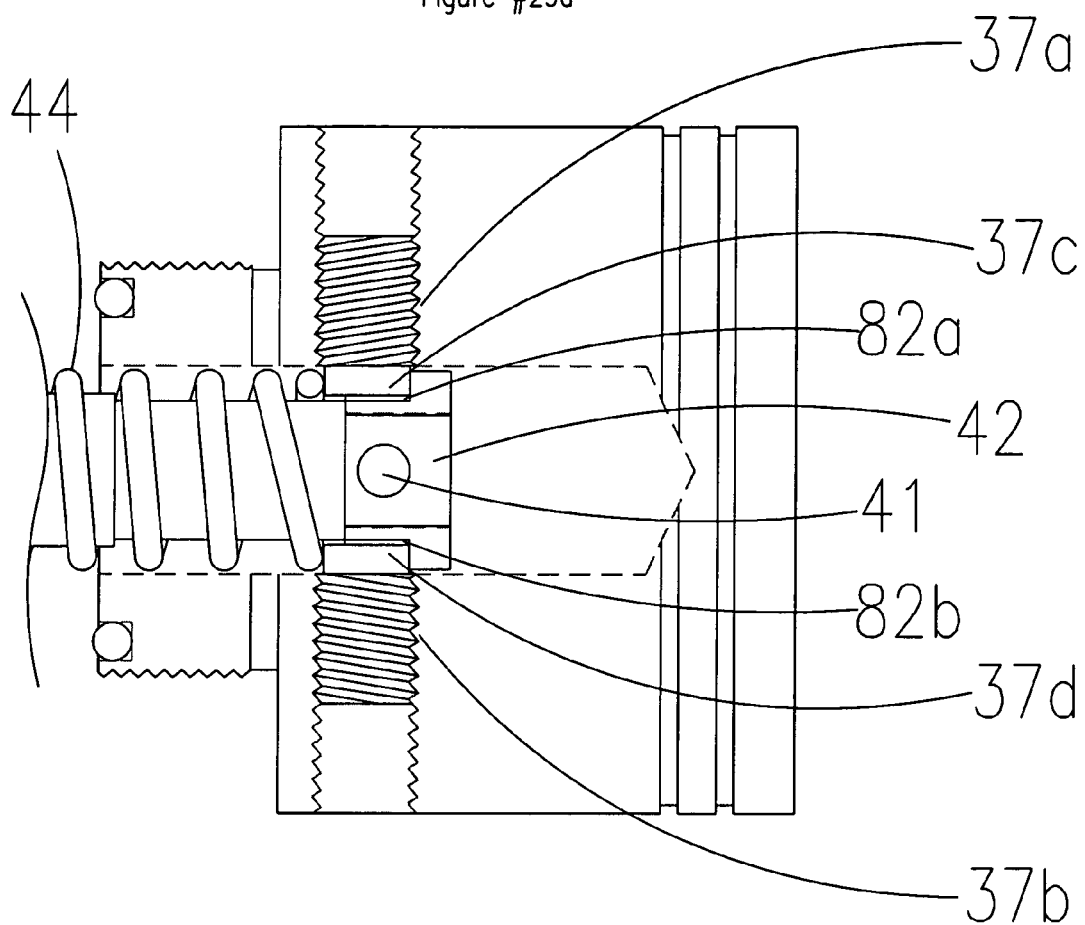
Figure #29a
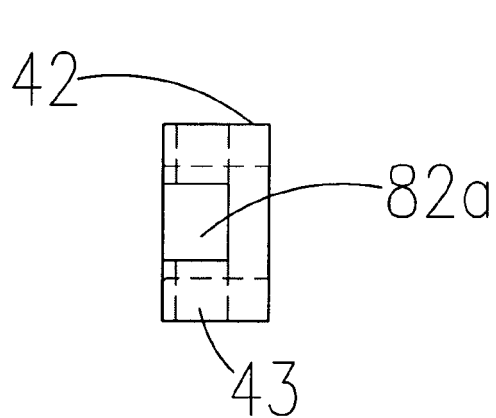
Figure #29b
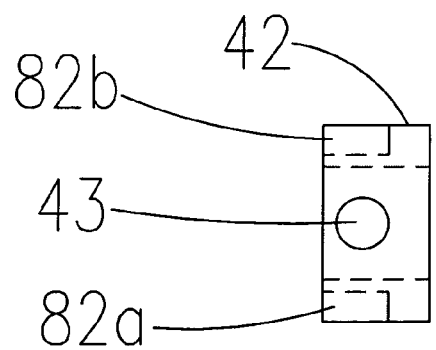
Figure #29c

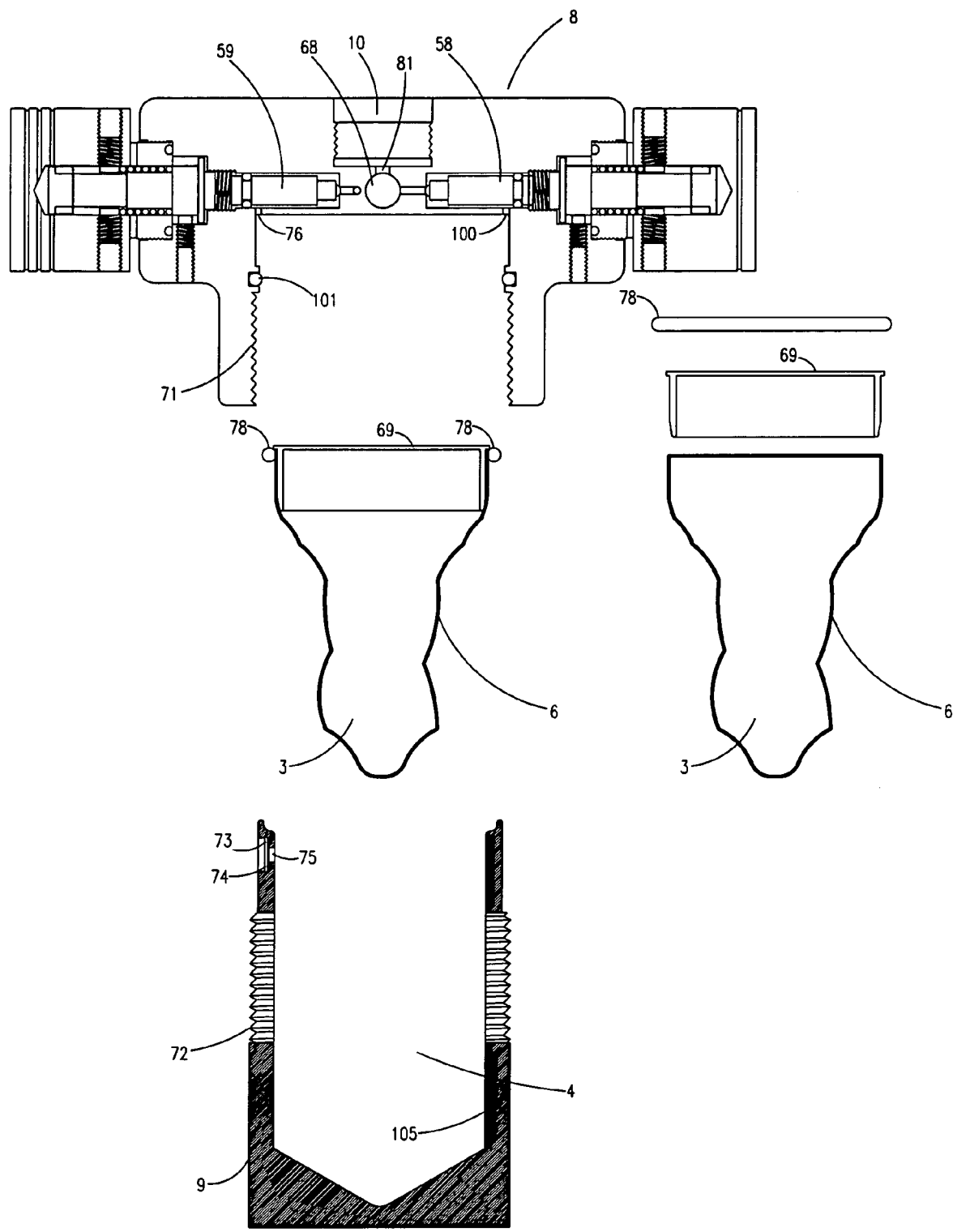
Figure #30

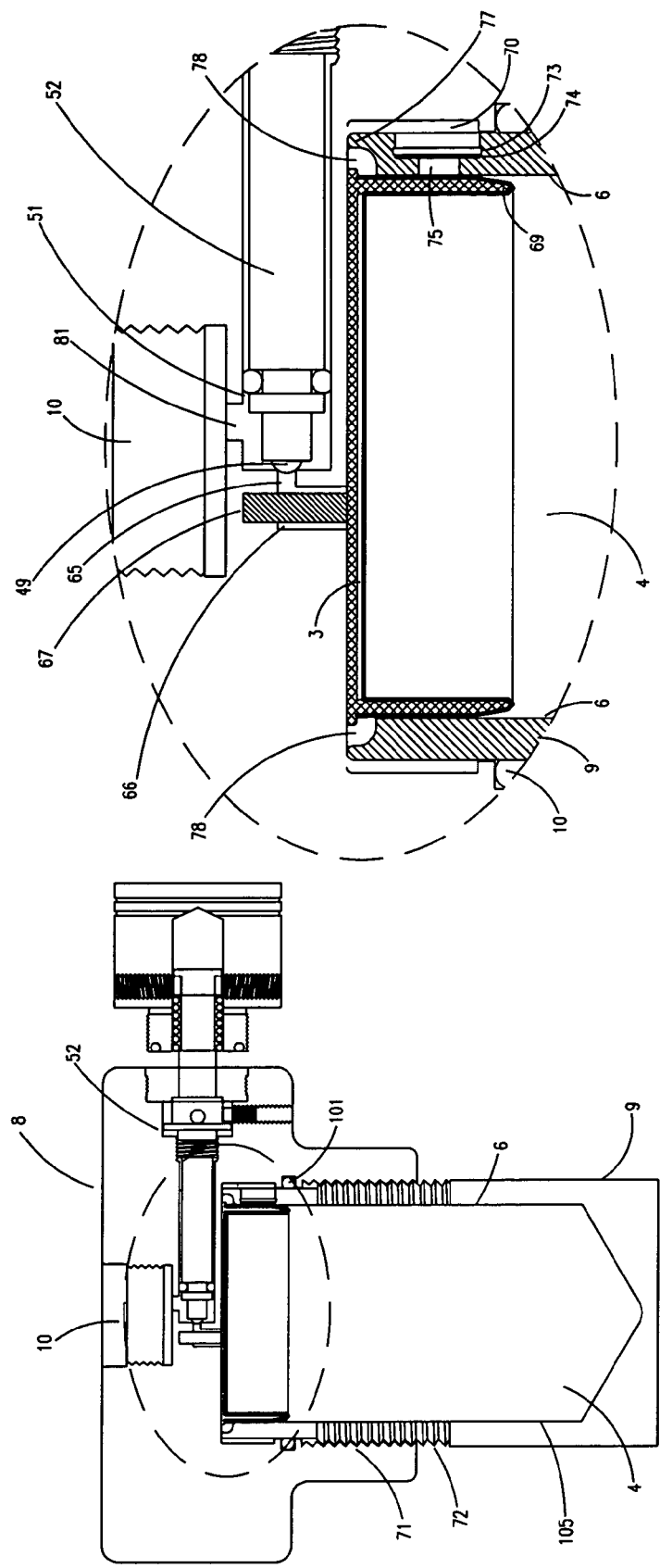
Figure #31

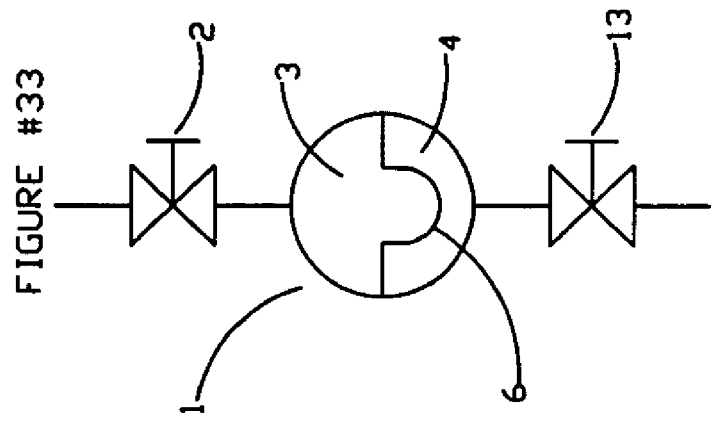
FIGURE #33
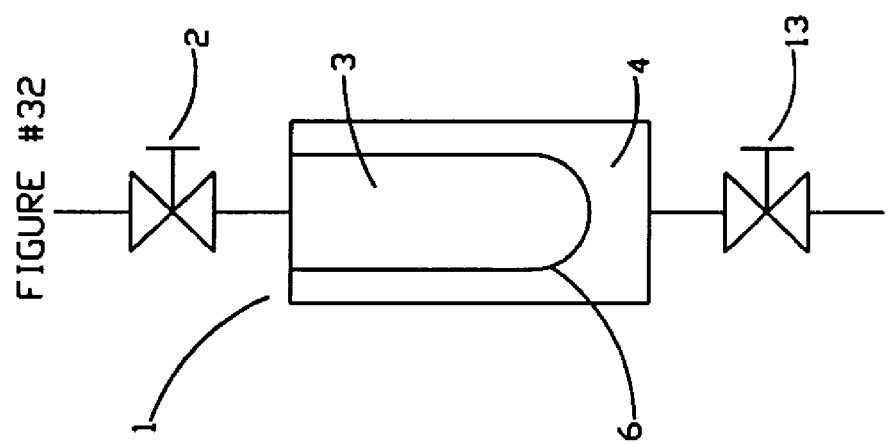
FIGURE #32

MULTI-CAVITY SAMPLE CYLINDER WITH INTEGRATED VALVING

PRIORITY CLAIM

The present application claims the benefit of U.S. Provisional Patent Application No. 60/400,736, having a filing date of Aug. 2, 2002 listing inventor Donald A. Mayeaux.

TECHNICAL FIELD OF THE INVENTION

The present invention relates to sampling of hydrocarbon fluid streams and devices therefore, and in particular to a system particularly suitable for obtaining a representative sample of a natural gas stream, which is at or below its hydrocarbon dew point temperature (H.C.D.P.). The preferred embodiment of the present invention contemplates a sample cylinder having a flexible isolation barrier and integrated valving to provide a controlled ingress of sample gas at nominal pressure differential. The system thereby avoids throttling of the sample gas and the inherent cooling problems associated therewith when the stream is at or below hydrocarbon dew point temperature. The flexible isolation barrier of the present invention is relatively inexpensive and is configured for quick and easy replacement, which may be routinely performed to insure sample integrity. Alternative embodiments of the invention contemplate a spherical sample cylinder configuration with flexible isolation barrier, as well as an improvement for piston-type sample cylinders to provide constant sample pressure.

GENERAL BACKGROUND OF THE INVENTION

Natural gas is a vital source of heat energy in the United States. Its selling price is based on volume and heat content. The heat content is greatly influenced by the presence of the heavy (higher molecular weight) components. These heavy components also have a large influence on the gases physical properties, which in turn impact flow rate calculations. The heat content and physical properties of gas are primarily determined by calculations based on gas composition.

The gas composition is determined by analysis on gas obtained by one or more of three means: spot sampling, composite sampling, and on stream (on line) analyzer sample systems. Spot sampling consists of extracting a natural gas sample at a point in time representing source gas composition at that point in time. The sample is stored in a sample container (sample cylinder).

Composite sampling consists of extracting very small increments of natural gas samples over a long period of time, usually one month, said samples being stored in a single sample container. The result is a composite of a sample gas representing the entire quantity of source gas, which flowed through the pipeline during the sampling period. Sample containers containing stored spot or composite samples are transported to a laboratory and analyzed for composition.

In the case of "on stream analyzer sample systems" a sample is withdrawn continuously or semi-continuously and routed directly into to an analyzer, usually a gas chromatograph, for real time analysis. It is well known by the natural gas industry that it is very difficult to obtain a representative sample of a natural gas stream, which is at or below its hydrocarbon dew point temperature (H.C.D.P.).

The American Petroleum Institute (API) Manual of Petroleum Measurement Standards, Chapter 14, Section 1 and Gas Processors Association's (GPA) Standard 2166, "Obtaining Natural Gas Samples for Analysis by Gas Chromatography", are good references for sampling of natural gas. Both organizations recognize the difficulty in sampling natural gas with high H.C.D.P. The GPA Standard 2166 outlines eight methods for spot sampling with sample cylinders. The API 14.1 standard provides further recommendations on the use of these methods.

The standards refer to several sources of error. Some of the most important are as follows:

1) Sampling a natural gas source containing liquid in any form. i.e.—The source gas is at or below its H.C.D.P. temperature.
2) Sampling a natural gas source at an ambient temperature that is below the H.C.D.P. temperature of the flowing gas source.
3) Throttling of the sample gas stream as it flows from the source to a sample container or on stream analyzer, especially if the throttling causes the temperature to drop (Joule-Thomson cooling effect) to near or below the gas H.C.D.P.

The importance of proper treatment of natural gas samples that are near or below their H.C.D.P. is the focus of the industry's attention, especially in light of the mining of natural gas from deeper reserves having higher H.C.D.P. temperatures and the increasing value of natural gas.

Major problems with spot and composite sampling are the accumulation of liquid in the sample container during the "purging" phase and depletion or accumulation of high molecular weight components during the sample filling phase.

During the purging phase of sampling, sample lines from the source to the sample container and the sample container itself are purged with sample gas to remove or displace residual gases. Most of all of the problems addressed by the eight GPA Sampling methods are related to the purging phase.

There are currently two basic types of sample containers (sample cylinders). One is the constant volume type, which is usually a small steel cylinder with fixed volume having valves at one or both sides. The second type is a constant pressure sample cylinder. This is a small steel cylinder having an internal "floating" piston, end caps at both cylinder ends, and valves in both end caps. The floating piston separates the internal cylinder volume into two cavities. The pressure in the two cavities is maintained at somewhat the same level by movement of the floating piston. For example, if the pressure in one cavity is raised above that of the other cavity, the floating piston is moved in the direction of the lower pressure cavity until the pressure in both cavities is somewhat equilibrated. This type of sample cylinder was designed to prevent "throttling" of sample gas.

After purging of exterior lines, pre-charge gas (gas stored at elevated pressure in one of the cavities before actual sampling begins) is released slowly. When the "pre-charge" gas pressure drops below the sample supply pressure, the piston moves towards the pre-charge cavity end of the cylinder allowing the sample gas to enter the sample cylinder without throttling.

Several problems are associated with the use of this type of hardware. One such problem is that the friction of the piston seals can cause a pressure difference of 20 to 30 PSI between the two cylinder cavities. The second is that the piston seals can harbor contaminates from previous samples. Cleaning is very difficult and time consuming. The entry ports and valving designs in the end caps require purging and also represent a source of sample composition distortion during the purging phase.

Constant volume cylinders are difficult to clean between samples as recommended by API and GPA standards. It is also difficult if not impossible to verify if they are indeed clean after the cleaning process.

Further, prior art valves typically installed on sample cylinders are prone to becoming damaged during transportation. The valve knobs are mounted on slender stems, which protrude from the valve body. The stems are often bent when cylinders are dropped or handled roughly. Valve stem packing leaks are also a common problem. Vibration and rough handling during transportation an also result in valves becoming partially opened thereby allowing fluids to leak out.

The prior art has therefore failed to provide a constant volume-type sample cylinder which is easy to clean and service, reliable in operation, and effective in preventing throttling of the sample gas.

GENERAL SUMMARY DISCUSSION OF THE INVENTION

Unlike the prior art, the present invention provides a system for obtaining a representative gas sample with a sample cylinder which allows for sampling with nominal pressure differential during sampling, so as to avoid the Jule-Thomson cooling effect, and thereby prevent liquification of parts of the sample due to a drop to or below hydrocarbon dew point pressure.

The preferred embodiment of the present invention contemplates a sample container, which may be a cylinder, sphere, or other confiruation, having a flexible isolation barrier and integrated valving to provide a controlled ingress of sample gas at nominal pressure differential. Throttling of the gas is thereby avoided.

Further, the flexible isolation barrier may be fabricated of an inert, relatively inexpensive, and easily handled material, and the cylinder is thereby designed for easy repair or replacement of the barrier component, which replacement may be routinely performed to insure sample integrity. Further, barriers of different materials may be changed out as required, depending upon the material in contact with the barrier.

In the preferred embodiment of the present invention, the sample cylinder is divided by the flexible isolation barrier, providing first and second cavities, the first cavity for receiving a fluid sample, the second cavity for providing pressure means (via pre-charging) commensurate with the ingress pressure of the sample gas, to provide controlled ingress of the sample gas into the first cavity.

An alternative embodiment of the present invention contemplates an improvement in piston-type sample cylinders to provide constant sample pressure, utilizing an improved valve ingress and discharge system to provide a more controlled sampling than prior art piston cylinder systems.

It is therefore an object of the present invention to provide a sample container having a flexible isolation barrier configured to receive sample fluids at nominal pressure differentials.

It is another object of the present invention to provide a method of sampling gas utilizing a flexible isolation barrier system.

It is another object of the present invention to provide an improvement in piston-type sample cylinders, providing a pressure equalization system to provide nominal pressure differentials during sampling.

It is another object of the present invention to provide a sample cylinder having a flexible isolation barrier which is easily and quickly changed to prevent contamination, or to provide an alternative barrier material as required.

Lastly, it is an object of the present invention to provide a method and system for sampling gas at or near the hydrocarbon dew point temperature which provides an accurate sample, while avoiding fluid formation due to gas throttling.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1 is a schematic view of a sample cylinder with a flexible isolation barrier attached in the middle.

FIG. 2 is a schematic view of a sample cylinder with a flexible isolation barrier totally expanded in cavity 3, with cavity 3 volume equaling zero and cavity 4 is at its maximum volume.

FIG. 3 is a schematic view of a sample cylinder with a flexible isolation barrier totally expanded into cavity 4, with cavity 4 volume equaling zero and cavity 3 is at its maximum volume.

FIG. 4 is a schematic view of a sample cylinder with a flexible isolation barrier totally expanded in cavity 3, with cavity 3 volume equaling zero and cavity 4 is at its maximum volume.

FIG. 5 is a schematic view of a sample cylinder of the head and bowl design of the present invention, with the flexible isolation barrier is attached in the head and internal flow paths are shown schematically.

FIG. 6 is a schematic view of a sample cylinder of the head and bowl design, with the flexible isolation barrier attached in the head and internal flow paths, wherein the cavity 3 volume equals zero and cavity 4 volume is at its maximum.

FIG. 7 is a schematic view of the sample cylinder of the head and bowl design, with the flexible isolation barrier attached in the head and internal flow paths are shown, and wherein cavity 4 volume is zero and cavity 3 volume is at its maximum.

FIG. 8 is a schematic, external view of the sample cylinder external profile with isolation barrier.

FIG. 9 is a side view of the flexible isolation barrier.

FIG. 10 is a top, cut-away view of the head of the system of the present invention, showing the integrated valves and some fluid passages, with the valves shown in their closed position.

FIG. 11 is a side, cut-away view of the sample cylinder of the present invention, illustrating the purge and vent valves, and end view of inlet valve.

FIG. 12 is a flow diagram for the initial sample cylinder preparation prior to sampling gas.

FIG. 13 is a top view, cut-away view of head of the present invention, wherein integrated valves and some fluid passages are shown, with the inlet and vent valves shown in their open position, and the purge valve is shown in a closed position.

FIG. 14 is a side, cut-away view of the inlet valve of the sample cylinder of the present invention, showing passages from inlet valve to cavity 3, as well as the pin in hole passage and flexible isolation barrier.

FIG. 15 is a close-up, cut-away view of the bowl rim and head area of the sample cylinder of the present invention.

FIG. 16 is a top, partially cut-away view of the head of the sample cylinder system of the present invention, illustrating the integrated valves and some fluid passages, with the vent and inlet valves are in a closed position, and the purge valve in a closed position.

FIG. 17 is a flow diagram illustrating the filling of the sample cylinder from a gas source.

FIG. 18A is a top view of the inlet port, inlet valve and purge valve of the head on the sample cylinder of the present invention, with the inlet valve and purge valve shown in closed position.

FIG. 18b is a top view of the inlet port, inlet valve and purge valve of the head on the sample cylinder of the present invention, with the inlet valve shown in a closed position, and the purge valve shown in an open position.

FIG. 18c. is a top view of the inlet port, inlet valve and purge valve of the head on the sample cylinder of the present invention, with the inlet valve shown in a open position, and the purge valve shown in an closed position.

FIG. 19 is a side, partially cut-away view of the sample cylinder flexible isolation barrier of the present invention totally collapsed against head surface, showing cavity 3 volume at zero, with cavity 4 volume is at its maximum.

FIG. 20 is a flow diagram of SAMPLE CYLINDER illustrating a sample being withdrawn to an analyzer.

FIG. 21 is a schematic of a sample cylinder having two flexible isolation barriers situated therein.

FIG. 22 is a schematic of a sample cylinder having two flexible isolation barriers situated therein, and a mechanical restraint portion having openings to permit fluid flow.

FIG. 23 is a schematic of a sample cylinder having two flexible isolation barriers situated therein, and a mechanical restraint partition without openings.

FIG. 24 is a side, partially cut-away view of an off-the-shelf constant volume cylinder equipped with a flexible isolation barrier and valving.

FIG. 25 is a flow diagram of an off-the-shelf constant volume cylinder equipped with a flexible isolation barrier and valving.

FIG. 26a is a side, exploded view of a valve assembly-exploded.

FIG. 26b is a side, partially cut-away view of an assembled Valve assembly.

FIG. 28a is a top, partially cut-away view of a valve showing the knob, knob lock, and flat face seal, wherein the knob is screwed into head.

FIG. 28b is a top, partially cut-away view of a valve showing the knob, knob lock, and flat face seal, with the knob unscrewed from the head.

FIG. 29a is a top, partially cut-away view of the knob and knob lock.

FIG. 29b is a close-up, partially cut-away, side view of the knob lock with slots.

FIG. 29c is a close-up, side view of the knob lock.

FIG. 30 is a side, partially cut-away view of head, bowl, flexible isolation barrier, retention ring, and o-ring of the present invention.

FIG. 31 is a side, partially cut-away view of the head, inlet valve, pin and hole for the flexible isolation barrier support, and the flexible isolation barrier.

FIG. 32 is a schematic of the cylindrical sample container with the flexible isolation barrier attached at one end.

FIG. 33 is a schematic view of the spherical sample container with the flexible isolation barrier attached near its middle.

DETAILED DISCUSSION OF THE INVENTION

Sample Cylinder Device

Figure 27:
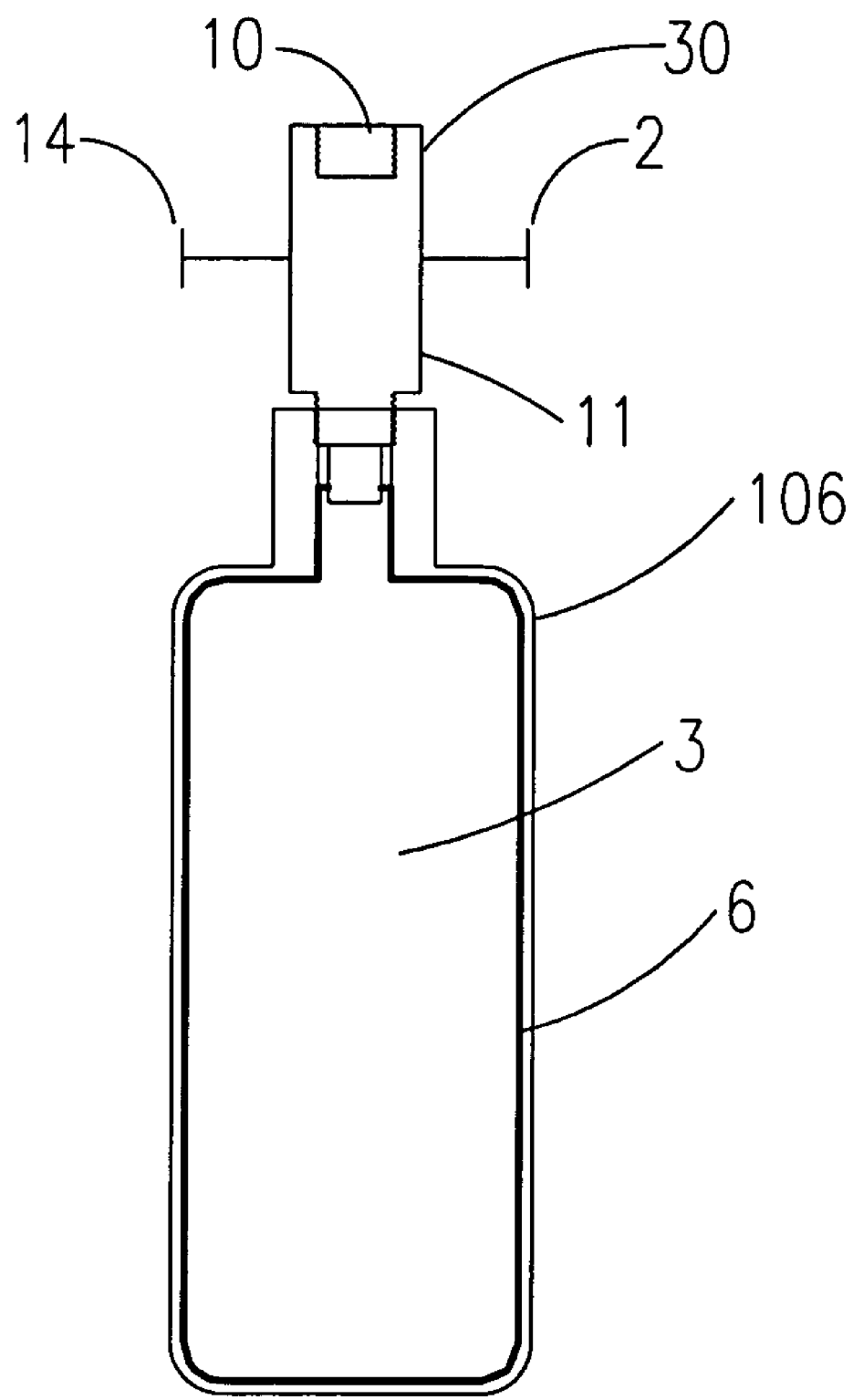
FIG. 27 is a side, partially cut-away view of a constant volume sample cylinder with the flexible isolation barrier liner of the present invention.

Referring to FIGS. 1–4, the first invention consists of a cylinder 1 forming the body of the unit, the cylinder having a chamber formed therein having a flexible isolation barrier 6 attached therein (FIG. 1). Flexible isolation barrier 6 divides the internal volume of the cylinder 1 into two sections or cavities (cavity 3 and cavity 4). Inlet valve 2 and purge valve 13 installed at each end of the cylinder 1 provide fluid communication between each of the two cavities and the exterior of the cylinder 1.

By first opening inlet valve 2 and then allowing a source of gas (pre-charge gas) to flow into cavity 4 by way of purge valve 13, the flexible isolation barrier 6 is moved toward cavity 3 thereby displacing the residual gas in cavity 3. When all of the gas is displaced, the flexible isolation barrier 6, being a thin and flexible material, conforms to the interior of the section of sample container formerly comprising cavity 3.

The volume of cavity 3 is now essentially zero (FIG. 2). After closing inlet valve 2, the cylinder 1 may be disconnected from the pre-charge gas source and brought to a field location where source gas is to be sampled. Purge valve 13 may be closed prior to disconnect if desired in which case the cavity 4 remains pressurized with pre-charge gas. This in some cases may be desired. In other cases, cavity 4 is depressurized to atmospheric pressure.

A source of gas to be spot sampled is first connected to purge valve 13. Opening purge valve 13 pre-charges cavity 4 to a pressure about equal to the source pressure. Depending upon the pre-charge gas pressure in cavity 4, gas flows from the source gas to cavity 4 or from cavity 4 to the source gas. Purge valve 13 is now closed and the source gas is now disconnected from purge valve 13 and connected to inlet valve 2. Inlet valve 2 is then opened.

Source gas will not flow initially through inlet valve 2 since the pre-charge pressure is equal to the source pressure at inlet valve 2. Purge valve 13 is now opened partially allowing pre-charge gas from cavity 4 to exit and flow to the atmosphere. As the pressure in cavity 4 tends to lower by venting in this manner source gas enters cavity 3 through inlet valve 2, the flexible isolation barrier 6 is moved toward cavity 4 which is now reducing in volume, but whose pressure is held constant at source pressure by the action of the flexible isolation barrier 6 movement.

The pressure differential between the two cavities is essentially zero since the flexible isolation barrier 6 material requires only a microscopic force to flex. During the filling process through inlet valve 2, the source gas is not throttled, but rather its flow is controlled by the egress of the flexible isolation barrier 6, which in turn is controlled by the flow rate of pre-charge gas through purge valve 13.

When the pre-charge gas is sufficiently discharged, the flexible isolation barrier 6 conforms to the interior surface of the former cavity 4, as shown in FIG. 3, and cavity 4 volume is essentially zero. Inlet valve 2 is closed and the sample container can now be brought to a laboratory for analysis of the sample gas. Purge valve 13 may be closed to insure that in the event of an flexible isolation barrier 6 failure, sample gas would not be vented through purge valve 13. However, functionally it does not need to be closed.

To analyze the sample gas in the cylinder 1, the analyzer sample system is connected to inlet valve 2. By opening inlet valve 2 sample gas flows to the analyzer. The sample gas pressure of cavity 3 will fall as sample gas flows out of it. If it were desired to control the cavity 3 pressure at a specific level then a source of auxiliary gas is connected to cavity 4 by way of purge valve 13. The auxiliary gas pressure is maintained by external means at the sample gas pressure desired in cavity 3. In a manner similar to that which occurred during the filing process auxiliary gas will fill cavity 4 as sample gas exits inlet valve 2 and the flexible isolation barrier 6 will retreat into cavity 3 until the cavity 3 volume is essentially zero as shown in FIG. 4.

The preceding describes the basic concept of a "constant pressure sample cylinder" construction by use of an flexible isolation barrier 6. The aforementioned (figures) are more indicative of fluid flow paths then of specific mechanical design. FIG. 5 show that a cylinder 1 may be designed such that all valving and porting is located at one end of the cylinder 1. This makes it easier to manufacture the cylinder 1 and substantially improves performance by minimizing the volume of source gas required for purging.

FIGS. 5–7 reflect the fluid flow path and FIG. 8 indicates the approximate physical location of the valves 2, 13, and 14, inlet port 10, and vent port 11 relative to the flexible isolation barrier 6 and cavities 3 and 4, wherein cavity 3 is situated interior isolation barrier 6, and cavity 4, exterior, the isolation barrier 6 having first, interior and second, exterior sides, in this application.

With this arrangement, (refer to FIGS. 5, 6, and 7) the pre-charging and sample filling of the cylinder 1 is as follows. The "vent" port 11 is connected to a pre-charge gas source. Purge valve 13 is closed, vent valve 14 open, and inlet valve 2 open. The inlet is at atmospheric pressure. By external valving means, pre-charge gas is admitted to cavity 4 by way of vent valve 14. The flexible isolation barrier 6 is moved toward cavity 3 displacing residual gas in cavity 3. The residual gas is vented from the cavity through inlet valve 2.

When essentially all of the residual gas is expelled in this manner and the flexible isolation barrier 6 conforms to the former cavity interior surfaces (FIG. 6), inlet valve 2 is closed, vent valve 14 is closed, and purge valve 13 remains closed. Cavity 3's volume is essentially zero and cavity 4, whose volume occupies essentially all of the cylinder 1 internal volume, is now filled with pre-charge gas. The pre-charge gas pressure can be very low (approximately 100 PSI); the exact pressure depends on the flexible isolation barrier 6 flexibility. It is not essential to retain the pre-charge gas pressure in cavity 4. The cylinder 1 can now be transported to a field location of source gas to be sampled.

The source gas is connected to the inlet port 10 and purge valve 13 is opened. The source gas is allowed to flow into cavity 4 by opening external valving in the source gas connecting line (not shown). After cavity 4 is pre-charged in this manner until its pressure is equal to the source gas pressure, purge valve 13 is closed and inlet valve 2 is opened. Source gas cannot flow into cavity 3 by way of inlet valve 2 until vent valve 14 is opened and pre-charge gas from cavity 4 is allowed to exit by way of vent valve 14 and vent port 11 to the atmosphere. Vent valve 14 is now opened and as previously described, the flexible isolation barrier 6 retreats into cavity 4 allowing source gas (sample gas) to flow into cavity 3 without throttling occurring.

All external sources of throttling are removed, such as the opening of valves and the pre-charge exit flow is kept to a minimum rate so as not to create a pressure drop in the source gas connecting piping or internal passages of the cylinder 1. When essentially all of the pre-charge gas is expelled from cavity 4 (FIG. 7) and source sample gas fills cavity 3, the flexible isolation barrier 6 conforms to the interior surfaces of former cavity 4 completing the filling process, then valves 2, 13, and 14 are closed. Cylinder 1 may now be disconnected from the source gas and transported to a laboratory for analysis.

At the laboratory or analyzer location, the analyzer's sample system is connected to the "inlet port" 10. Inlet valve 2 is opened and sample gas from cavity 3 is allowed to flow into the analyzer sample system. The flow rate is controlled by the analyzer sample system (not shown). If it is desired to maintain the gas pressure at a specific level in cavity 3, then as previously described, an auxiliary gas, applied to cavity 4 by way of vent valve 14, can be used to maintain the desired pressure. There are many variations of the purging, pre-charging, filling, and sample extraction from the cylinder 1 for analysis. The foregoing explanation describes the general spirit of hardware design and gas flow.

Cylinder with Integrated Valves

Continuing with FIGS. 7–11, another important aspect of this invention is the specific hardware design. For example, inlet valve 52, purge valve 58 and vent valve 59 (FIGS. 8, 9, 10, and 11) are integrated into the head 8 as well as the inlet port 10 and vent port 11. Inlet valve 52 is designed into this structure such that when it is in a closed position there is essentially zero volume between the flexible isolation barrier 6 when fully retracted into cavity 3, (FIGS. 10 & 31), and inlet valve 52.

That means that cavity 3, which will ultimately contain the sample gas is essentially zero and therefore does not need to be purged. Recall that great sources of problems and errors occur during the purging of sample containers of prior art. An object of this invention is to reduce or eliminate the source of purging errors by eliminating the requirement for purging the sample gas containing cavity.

Internal passages also provide for sample gas flowing into the inlet port 10 from an outside source to sweep or purge the volume on the upstream side of inlet valve 52 (all volume between the inlet port 10 and inlet valve 52). Refer to FIGS. 11, 13, & 14. Therefore in the aforementioned description of when source sample gas is flowing through the inlet port 10 and purge valve 58 to pre-charge cavity 4, essentially all of the volume upstream of inlet valve 52 is purged. In other variations of the invention's design, gas, which is removed from cavity 4 to allow filling of cavity 3, will be contained in a third cavity (cavity 16) [FIGS. 21, 22, and 23].

This design "measures" the amount of source gas used for purging in the sense that pre-charging of cavity 4 requires a specific volume of pressurized gas. If external piping should require additional purging, then the pre-charge gas can be vented by opening vent valve 59. Vent valve 59 is then closed and the pre-charging step repeated as many times as required. Prior art hardware does not limit the purging; therefore, technicians are prone to excessive purging which can result in sample composition distortion errors.

In another variation of this invention cavity 16, formed by flexible isolation barrier 15 (FIG. 21) is filled with an inert or non-harmful gas. During the purging of the external sample delivery and cylinder 1 internal passages flexible isolation barrier 6 is fully collapsed and by admitting sample gas into cavity 4 by way of valve 13. At this point, cavity 3 has essentially a zero volume. During the filling of cavity 3 with sample gas, the gas from cavity 16 is released allowing cavity 4 to depressurize. In that case only non-harmful gas is released to the atmosphere. Potentially harmful gas in cavity 4 may be disposed of at a later time in a safe area.

Initial Cylinder Preparation Prior to Sampling Gas

Cylinder 1 is connected to a gas source 87 and four way valve 90 as shown in FIGS. 12, 13, 14, and 15. With a new or clean flexible isolation barrier 6 installed in cylinder 1, vent valve 59 and purge valve 58 are closed, inlet valve 52 is opened and valve 90 is actuated in a position in which its internal flow is represented by solid lines (i.e.—no flow through dashed lines).

Vent valve 59 is then opened (FIG. 13) allowing source gas 87 (FIG. 12) to flow through pressure regulator 88 line 89 into port 90*a* and out of port 90*b* of valve 90, through line 99 into port 11, passage 64, vent valve cavity 60, passage 76, into head/bowl annulus 70 (FIG. 15), frit 74, passage 75 an into cavity 4.

This causes flexible isolation barrier 6 to fold up thereby forcing gas from cavity 3 through passage 66 (FIG. 14) and passage 65, into inlet cavity 51 passage 81, inlet port 10, line 98, entering valve 90 at port 90*d* and exiting through port 90*c* and then to the atmosphere or a safe vent 91. When flexible isolation barrier 6 is completely collapsed and the volume of cavity 3 is essentially zero, then vent valve 59 and inlet valve 52 are closed. The only remaining gas in cavity 3 is the microscopic amount (approximately 0.005 cubic centimeters) trapped between the flexible isolation barrier 6 and inlet valve ball, FIGS. 10, 14, and 16, in passages 66 and 65.

This small volume of trapped gas, usually at or near atmospheric pressure, is diluted when cavity 3 is later filled with sample gas which produces an insignificant amount of contamination. If in special cases even this small amount of contamination cannot be tolerated, then at this point in time, cavity 3 is filled with helium then vented until its volume is again essentially zero (approximately 5 micro liters). This dilutes the trapped gas, depending on the helium gas pressure supplied to cavity 3, by a factor of approximately one million to one. This dilution step is performed by rotating valve 90 to its second position wherein its internal flow is indicated by dashed lines (FIG. 12). Inlet valve 52 and vent valve 59 are opened allowing source gas 87 to flow through regulator 88, line 89 into port 90*a* and exit of port 90*d* into line 98, inlet port 10, passage 81, cavity 51, passage 65, passage 66 into cavity 3. The flexible isolation barrier 6 expands forcing gas from cavity 4 to flow through passage 75, frit 74, annulus 70, passage 76, vent valve cavity 60, passage 64, vent port 11, line 99, into port 90*b*, out of port 90*c* to the atmosphere or safe vent area 91.

When flexible isolation barrier 6 is fully expanded and the volume of cavity 4 is essentially zero and the volume of cavity 3 is at its maximum, valve 90 is actuated to its former position wherein its internal flow is indicated by solid lines. Supply gas 87 again flows into cavity 4 and the gas contents of cavity 3 flows to the atmosphere or safe vent area 91 as previously described. When flexible isolation barrier 6 is fully collapsed and the volume of cavity 3 is essentially zero, then inlet valve 52 and vent valve 59 are closed and lines 98 and 99 disconnected from cylinder 1. Cylinder 1 is now ready to be utilized for obtaining a gas sample.

Sampling a Gas Source

With vent valve 59, inlet valve 52, and purge valve 58 closed, line 84 (FIGS. 14, 15, 16, 17, and 19) is connected to cylinder 1 inlet port 10. Valve 85 and purge valve 58 are opened allowing gas from source 83 to flow through valve 85, line 84 inlet port 10, passage 81, inlet valve cavity 51, passage 63, purge valve cavity 54, passage 100, annulus 70, frit 74, passage 75, and into cavity 4. Gas flows into cavity 4 until its pressure is equal to the gas source 83 pressure. The filling of cavity 4 in this manner has swept or purged the external sample delivery system, inlet port 10, passage 81, and inlet valve cavity 51 with sample gas.

A representative sample of the gas source 83 is present in inlet valve cavity 51. Purge valve 58 is closed, then inlet valve 52 and vent valve 59 are opened. Gas from source 83 then flows into inlet port 10, passage 81 (FIGS. 11, 13, 14, 15, and 17), inlet valve cavity 51, passage 65, passage 66, into cavity 3. Flexible isolation barrier 6 unfolds and gas from cavity 4 flows through passage 75, frit 74, annulus 70, passage 76, vent valve cavity 60, passage 64, vent port 11, then to the atmosphere or a safe area.

Volume between the collapsed flexible isolation barrier 6 and ball 49 of inlet valve is essentially zero (approximately 5 micro liters) cavity 3 requires no purging. That eliminates the largest source of sampling error in filling sample gas cylinders.

If the residual volume is excessive for some rare applications, it may be diluted with helium during the precharging of cavity 4 as previously described. In the case of natural gas wherein the analysis is typically performed by Gas Chromatographs which utilize Helium as a carrier gas, the Helium will not be detected. In that case, all components of the sample gas are normalized to a total of 100%. Normalizing in this manner is a common practice.

Inlet valve 52, and vent valve 59 are then closed and line 84 of the external sample delivery system is disconnected. Cylinder 1 may now be transported to a laboratory for analysis of its sample gas contents. During the filling of cavity 3, throttling of the sample gas was avoided as a means for controlling the gas flow rate. Instead the gas flow rate entering cavity 3 was actually controlled by the flow rate of gas being vented from cavity 4 through vent valve 59. This process is ideal in several ways. First, even though throttling were to occur in the internal passages of cylinder 1, leading into cavity 3, and the resulting Joule-Thomson cooling effect were to cool the gas below its dew point resulting in condensation, it would not impact the composition of gas in cavity 3. This is because all of the gas entering inlet valve 52 passes into cavity 3.

This eliminates the problems caused by the purging of prior art cylinders. Secondly, the Joule-Thomson cooling effect from throttling of vent valve 59 results in cooling of gas vented from cavity 4. This does not result in the cooling of cylinder 1 or the gas being sampled.

Third, even though the entire Joule-Thomson cooling effect were applied to cylinder head 8 when releasing gas contents pressurized at 2000 PSI the net result is less than 0.1 degree Fahrenheit change in this temperature of head 8.

Removing Sample Gas from the Cylinder

Sample line 94 (FIG. 20) is connected to inlet port 10 and analyzer 95. When inlet valve 52 is opened, gas flows from cavity 3 through passage 66 (FIG. 14), passage 65, inlet valve cavity 51, passage 81, inlet port 10 and line 94 to analyzer 95. Sample flow and pressure regulation components integral to analyzer 95 are not shown.

Optionally a source of gas may be utilized to maintain a constant pressure in cavity 3 as it discharges into the analyzer. To accomplish this, a gas source 92 (FIG. 20) supplies gas through pressure regulator 96, line 93 to vent port 11. Opening vent valve 58 allows the gas source to then flow into cavity 4 by paths previously described. The pressure of cavity 3 is controlled by the pressure of gas in cavity 4 since flexible isolation barrier 6 deflects in response to any difference in pressure between the two cavities. Upon completion of analysis, lines 93 and 94 may be disconnected after first closing inlet valve 52 and vent valve 58.

Cylinder Design Variations

There are other variations of methods for utilizing the inventions as well as hardware design that are obvious to one skilled in this art. For example, FIGS. 1 & 33 show the attachment of the flexible isolation barrier 6 at two different points within the interior of the cylinder 1: one at the top (FIG. 32) and one at the approximate center (FIG. 1). Another variation is shown in FIG. 33 whereby the cylinder 1 is somewhat spherical as opposed to a cylindrical shape.

In FIG. 21, flexible isolation barriers 6 and 15 are shown. By use of appropriate valving a duplicate sample can be obtained in cavities 16 and 3 while using cavity 4 for pre-charging. This is useful for analyzing one sample and "retaining" a second sample for future analysis in the event of a disputed analysis in custody transfer applications. There may be many other reasons to obtain duplicate samples or two samples of different sources or same source at two different conditions or periods of time. Alternatively, vented sample fluids could be selectively released into the second cavity or chamber via a rupture disc.

In FIG. 22, a mechanical restraint 17 limits the travel of flexible isolation barriers 6 and 15. The mechanical restraint 17 has passages, which permits pre-charge gas to pass between cavities 22 and 23. This permits the volume of cavities 3 and 16 to become "fixed."

In FIG. 23, a partition 25 physically divides the cylinder 1 into two sections internally. Pre-charge gas cannot flow through partition 25. Pre-charge gas can only flow between cavities 27 and 26 via transfer valve 24. This physical arrangement provides a wide choice of purging, pre-charging, filling, and discharging techniques or methods. It is essentially two independent sample containers. Vent valve 13 and vent valve 35 provide means for gas to flow into and out of cavities 27 and 26 respectively.

The aforementioned hardware of FIGS. 1–8 can be used to sample source gas at atmospheric pressure or sub-atmospheric pressure. This is accomplished by evacuating cavity 4 with cavity 3 at zero volume condition. When the "inlet valve" 2 is opened, low-pressure gas from an external source is drawn into cavity 3 by the action of the flexible isolation barrier 6 retreat toward cavity 4. When it is desired to discharge the sample gas for analysis, cavity 4 can be pressurized to displace the flexible isolation barrier 6 thereby pressurizing sample gas in cavity 3 which then can be discharged through inlet valve 2 (FIG. 1).

When pre-charging, purging and filling cavity 3 and 27 in the upper portion of the cylinder 1 in FIG. 23, it is possible to "vent" the pre-charge gas into cavity 26 during the filling of cavity 3. This would eliminate the discharge of sample gas to the atmosphere. This is very important, especially when sampling toxic gas. There are other variations of the hardware design and techniques for their use, which should be obvious to those skilled in the art.

Another invention is the use of a flexible isolation barrier 6 in a sample container of the "constant volume" type. The constant volume sample containers have been in use for many years for sampling gases and liquids. In FIG. 24 it can be seen that a conventional constant volume cylinder 32 has been outfitted with a plug 31 at the lower and at the other end with a special valving arrangement having an flexible isolation barrier 6 attachment. As can be seen in the flow diagram of FIG. 25, the valving and cavity arrangement form flow paths and storage cavity relationships equal to that of the "head 8" and "bowl 9" arrangements previously discussed.

Therefore, constant volume cylinders of prior art may now be retrofitted as shown in FIG. 24 and used as previously described for the "head 8" and "bowl 9" design. New constant volume cylinders of prior art design may also be fitted and used as described. The valving arrangement of FIGS. 24 and 25 is designed such that the pre-charging gas cavity 4 sweeps (purges) the entire inlet port 10 and inlet valve 2 area in a similar manner as previously descried for the "head 8" and "bowl 9" designs. It can be readily seen that liquids, slurries, liquefied gases and other fluids may be sampled in a similar manner as previously described for gases. As shown in FIG. 27, the flexible isolation barrier 6 can be attached to a constant volume sample cylinder 106 in a manner that it functions as a liner or barrier to isolate sample fluids contained in said sample cylinder from the interior sample cylinder interior surfaces.

The flexible isolation barrier 6 is constructed of a thin flexible material, which is preferably inert and does not permeate any fluids of interest into the sample gas or pre-charge gas. Although many materials may be utilized for construction of flexible isolation barrier 6, a material of choice utilizes "Tedlar"® brand polyvinyl fluoride, which is manufactured by Dupont. It has been utilized for many years in the construction of sample bags for collecting and storing environmental samples and therefore has a good "history". Many other polymeric materials and elastomers may also be used. To reduce or eliminate diffusion of small molecules (such as Helium or Hydrogen) through the flexible isolation barrier 6, the material of construction may be coated or metalized.

By using the flexible isolation barrier 6 in a cylinder 1 construction, as previously described, the "sample fluid" does not contact the interior surface of the cylinder 1 bowl 9. Only a very small amount of surface in the "head 8" is contacted by sample fluid. When the cylinder 1 is designed as previously shown, the "head 8" is bolted or screwed to the "bowl 9".

When the "head 8" and "bowl 9" are unbolted (or unscrewed) and separated the flexible isolation barrier 6 is easily accessed for inspection or replacement. The interior surface of the "head 8", valving, and fluid passages may be easily accessed for cleaning. In practice, the flexible isolation barrier 6 may be removed and replaced with a new clean one.

The "head 8" is easily cleaned in a fluid bath by either wiping or another suitable means. This arrangement eliminates the cleaning problem associated with prior art constant volume and constant pressure cylinders.

The entry points to cavity surfaces of the cylinder 1 are designed to prevent damage to the flexible isolation barrier 6 when made to conform to an interior surface at said entry points. The entry point consists of either one or more small holes or a porous material such as sintered plastic or metal. A third preferred method of entry/exit passage is a pin in hole construction as can be seen in FIGS. 14 and 16. In that case the annulus (passage 66) is formed around the exterior pin 67 surface and the interior of the hole that the pin 67 is pressed in.

It can be readily seen that a change of hardware arrangement is possible without changing the spirit of the described invention. Valving may be positioned at either or both ends to effect the same or similar flow arrangement without changing the spirit of the invention.

In summary, the use of flexible isolation barrier 6 and cavities as shown in general, combined with the filling, pressurizing, evacuation, and discharge of fluids in the sample cylinder 1 made possible by the aforementioned hardware, provides by intention, a vast number of options for sampling fluids.

Constant Pressure Sample Cylinder

Prior art designs of constant pressure sample cylinders have valving integrated into one or both end pieces of the sample cylinder. The valving of prior art constant pressure cylinders require large amounts of fluid to purge the volume upstream of the inlet valve. The valving also does not provide a near zero volume space between the inlet valve and the floating piston.

This requires purging of said space to remove residual fluid. Integrated valving, as previously described for application to flexible isolation barrier equipped cylinders may be applied to current art constant pressure cylinders having floating pistons.

The purge (pre-charge) valve and inlet valve can be designed in such a manner that gas flowing into the precharge end of the cylinder sweeps or purges the entire external sample delivery system and all internal passages upstream of the inlet valve. This is similar to the relationship between inlet port 10, purge valve 58, and inlet valve 52 shown in FIG. 10. The floating piston and internal cylinder head inner surface can the be designed in a manner that produces essentially zero dead volume between the floating piston and inlet valve when the floating piston is fully retracted to the integrated valve end of the cylinder. This is similar to the relationship between flexible isolation barrier 6, and inlet valve 52 (FIG. 14).

Integrated Valve

Inlet valve 52, purge valve 58, and vent valve 59 (FIG. 10) are designed to provide a low internal valve volume, zero dead or unswept volume, protection against stem damage, and a backup seal to prevent fluid leakage during transportation.

The three aforementioned valves are of the same design, each having only slight variations to accommodate their specific functions. Therefore the following description of inlet valve 52 design is also applicable to the purge valve 58 and vent valve 59 designs. Inlet valve assembly 52 consists of (FIG. 26A), ball 49, o-ring 48, valve stem 45, recessed stem tip 97 to receive ball 49, o-ring groove 102 to receive o-ring 48, male threads 47a, shoulder 50, screw 46, spring 44, knob lock ring 42 having a hole 43, pin 41, o-ring 40, knob 36, male thread 38, o-ring groove 39 to receive o-ring 40, screw 37a having a dog point tip 37c, and screw 37b having a dog point tip 37d.

Inlet valve assembly 52 is assembled as shown in FIG. 26b. Knob lock 42 is fastened to stem 45 by the insertion of pin 41 through hole 43 and hole 104. Inlet valve is installed in Head 8 as shown in FIGS. 27, 28a, and 29b.

As shown on FIG. 28A and FIG. 10, the inlet valve assembly 52 is engaged in the fully closed position with ball 49 providing a seal against seat 56 (FIG. 10). The rotation of valve stem 45 in conjunction with male thread 47a and female thread 47b provide the linear travel required to seat and unseat ball 49 against seat 56. Male threads 38a and female threads 38b are shown fully engaged in FIG. 28a.

O-ring 40 in contact with surface 5 provides a seal for stem 45. Should the aforementioned seal fail, then fluids will be contained by the secondary flat faced seal formed by o-ring 40 in contact with surface 5 (FIG. 28a). In the position shown in FIG. 28a and FIG. 10, knob 36 is not mechanically engaged to stem 45. Therefore any hard blows to knob 36 resulting from rough handling would not either damage stem 45 nor rotate stem 45 in a manner which would result in disrupting the seal formed by ball 49 against seat 56. This is a safety feature and one which protects the environment.

To actuate inlet valve 52 to its open position (FIGS. 28b and 13) requires first rotating knob 36 to disengage male threads 38a from female threads 38b. After the threads are disengaged, spring 44 forces knob 36 away from head 8. Knob 36 is then rotated in any direction until dog point tips 37c and 37d of screws 37a and 37b enter slots 82a and 82b (FIGS. 28b, 29a, 29b, and 29c) of knob lock 42. This mechanically locks knob 36 to stem 45. Thereafter rotation of knob 36 will actuate valve 52 to its open and closed positions. To protect the valve stem 45 from damage and to contain any fluid leaks which might occur from failure of stem seal formed by o-ring 48 and surface 103 (FIGS. 10, 28a and 28b) the knob is pushed inward until male threads 38a contact female threads 38b at which point dog points 37c and 37d are out of slots 82a and 82b and knob 36 is mechanically disengaged from stem 45. Rotating knob 36 will not rotate stem 45 at this point.

Male threads 38a are then engaged tightly into female threads 38b (FIG. 28a) which provides protection for stem 45 and restores o-ring 40 seal to surface 5 (FIG. 10).

Replacing the Flexible Isolation Barrier

Instead of using an elaborate cleaning procedure to eliminate contaminates on the cylinder interior surfaces 105 (FIG. 30) as required by current art cylinders the flexible Isolation Barrier 6 is removed and replaced with a clean one. This is accomplished by unscrewing bowl 9 from head 8 and removing the flexible isolation barrier retention ring 69 with attached flexible isolation barrier 6 and o-ring 78 as shown in FIG. 30. O-ring 78 is then removed from retention ring 69 after flexible isolation barrier 6 is removed from retention ring 69. A clean flexible isolation barrier 6 is then inserted over retention ring 69 and o-ring 78 is installed over flexible isolation barrier 6 and retention ring 69. The flexible isolation barrier 6, retention ring 69, and o-ring 78 assembly is then lowered into bowl 9 and head 8 replaced by screwing on bowl 9. O-ring 101 seals head 8 and bowl 9. As shown, the isolation barrier 6 is formed to provide a mouth M to provide the opening to the interior containment area for the sample gas.

O-ring 78 forms a seal (see FIG. 15) between bowl rim 77, head inner surface 80, retention ring shoulder 79 and flexible isolation barrier 6. Shoulder 79 is forced downward by head surface 80 causing o-ring 78 to displace against all of the aforementioned sealing surfaces.

Referring to FIGS. 1–33, the elements of the invention are summarized as follows:

| Description | Element # |
| --- | --- |
| Container for Gases | 1 |
| Inlet Valve A | 2 |
| Cavity A | 3 |
| Cavity B | 4 |
| Surface | 5 |
| Flexible Isolation Barrier A | 6 |
| Vent Valve | 7 |
| Head | 8 |
| Bowl | 9 |
| Inlet Port | 10 |
| Vent Port | 11 |
| Inlet Valve A Knob | 12 |
| Purge Valve | 13 |
| Vent Valve | 14 |
| Flexible Isolation Barrier-B | 15 |
| Cavity C | 16 |
| Mechanical Restraint | 17 |
| Partition | 18 |
| Cavity D | 19 |
| Inlet Valve C | 20 |
| Cavity B-1 | 22 |
| Cavity B-2 | 23 |
| Transfer Valve | 24 |
| Solid Partition | 25 |
| Cavity D | 26 |
| Cavity E | 27 |
| Purge Valve Knob | 28 |
| Vent Valve Knob | 29 |
| Integrated Valve Assembly | 30 |
| Plug | 31 |
| Constant Volume Cylinder | 32 |
| Purge Valve Assembly | 33 |
| Vent Valve Assembly | 34 |
| Purge Valve | 35 |
| Inlet Valve Knob | 36 |
| Knob Retention Screw | 37a |
| Knob Retention Screw | 37b |
| Knob Retention Screw Tip | 37c |
| Knob Retention Screw Tip | 37d |
| Knob Male Threads | 38a |
| Knob Female Threads | 38b |
| O-ring Groove | 39 |
| O-ring | 40 |
| Knob Lock Pin | 41 |
| Knob Lock Ring | 42 |
| Hole | 43 |
| Spring | 44 |
| Inlet Valve Stem | 45 |
| Screw | 46 |
| Male Stem Thread | 47a |
| Female Stem Thread | 47b |
| O-ring | 48 |
| Ball | 49 |
| Stem Shoulder | 50 |
| Inlet Valve Cavity | 51 |
| Inlet Valve Assembly | 52 |
| Purge Valve Stem | 53 |
| Purge Valve Cavity | 54 |
| Ball | 55 |
| Inlet Valve Seat | 56 |
| Purge Valve Seat | 57 |
| Purge Valve Assembly | 58 |
| Vent Valve Assembly | 59 |
| Vent Valve Cavity | 60 |
| Vent Valve Ball | 61 |
| Vent Valve Seat | 62 |
| Inlet Valve/Purge Valve Passage | 63 |
| Vent Valve/Vent Port Passage | 64 |
| Inlet Valve/Cavity 3 Port Passage | 65 |
| Cavity 3 Port Passage | 66 |
| Cavity 3 Port Passage Pin | 67 |
| Cross-sectional end view of inlet valve stem | 68 |
| FIB retention o-ring | 69 |

-continued

| Description | Element # |
| --- | --- |
| Head/Bowl Annulus | 70 |
| Head Female Threads | 71 |
| Bowl Male Threads | 72 |
| Frit Retention Clip | 73 |
| Frit | 74 |
| Cavity 4 Passage | 75 |
| Head/Bowl Annulus to Vent Valve Cavity Passage | 76 |
| Bowl Upper Rim | 77 |
| Head/Bowl O-ring | 78 |
| FIB Retention ring Shoulder | 79 |
| Head Inner Surface | 80 |
| Inlet Port/Inlet Valve Cavity Passage | 81 |
| Knob Lock Slot | 82a |
| Knob Lock Slot | 82b |
| Pipeline | 83 |
| Sample Line | 84 |
| Sample Line Valve | 85 |
| Sample Probe | 86 |
| Pre-charge Gas Supply | 87 |
| Pre-charge Gas Supply Pressure Regulator | 88 |
| Supply Line | 89 |
| 4 Way Valve | 90 |
| 4 Way Valve Port | 90a |
| 4 Way Valve Port | 90b |
| 4 Way Valve Port | 90c |
| 4 Way Valve Port | 90d |
| Vent to Atmosphere or Safe Area | 91 |
| Gas Supply | 92 |
| Sample Line | 93 |
| Sample Line | 94 |
| Analyzer | 95 |
| Pressure Regulator | 96 |
| Valve Stem Tip Recess | 97 |
| Line | 98 |
| Line | 99 |
| Head/Bowl Annulus to Vent Cavity Passage | 100 |
| Head/Bowl O-ring | 101 |
| O-ring Groove | 102 |
| Surface | 103 |
| Hole | 104 |
| Surface | 105 |
| Constant volume sample cylinder with the flexible isolation barrier liner | 106 |

In summary, a method of the present invention may comprise the steps of:

a. providing a sample cylinder, having a body having a chamber formed therein;

b. providing a flexible isolation barrier, and utilizing said flexible isolation barrier to selectively divide said chamber in fluid impermiable fashion into first and second cavities;

c. forming a first passage associated with said first cavity for selectively allowing the passage of a sample fluid therethrough;

d. forming a second passage associated with said second cavity for selectively allowing the passage of a pre-charge fluid therethrough;

e. allowing a flow of pre-charged gas through said second passage, so as to urge said isolation barrier toward said first cavity, displacing residual gas in said first cavity;

f. pressurizing said second cavity via said second passage with a pre-charge gas at a pre-determined pressure;

g. flowing a sample gas at said pre-determined pressure though said first passage and into said first cavity;

h. utilizing said flexible isolation barrier, receiving about equal pressure from said pre-charge gas from said second cavity, to prevent throttling of said sample gas entering said first cavity; while i. providing controlled flow of said sample gas into said sample cylinder by selective venting of said pre-charged gas from said second chamber, until said said pre-charge gas is depleted from said second cavity, said flexible isolation barrier conforms to the interior of said chamber, and said sample gas fills said chamber of said sample cylinder.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A sample cylinder, comprising:
   a body having a chamber formed therein;
   a flexible isolation barrier situated within said chamber, said flexible isolation barrier selectively dividing said chamber into first and second cavities;
   an inlet valve associated with said first cavity; and
   a purge valve associated with said second cavity;
   whereby, upon allowing a flow of pre-charge gas through said purge valve, said isolation barrier is urged toward said first cavity, displacing residual gas in said first cavity, with said flexible isolation barrier conforming to the interior of said first cavity; and
   whereby, upon pressurizing said second cavity via said purge valve with a pre-charge gas at a pressure, and flowing a sample gas through said inlet valve and into said first cavity, said flexible isolation barrier, receiving pressure from said pre-charge gas from said second cavity, provides controlled flow of said sample gas into said sample cylinder via selective venting of said pre-charge gas from said second chamber, until said pre-charge gas is depleted from said second cavity, said flexible isolation barrier conforms to the interior of said chamber, and said chamber is filled with said sample gas.

2. The sample cylinder of claim 1, wherein said inlet valve is situated adjacent to said first cavity such that when said isolation barrier is urged toward said first cavity by said flow of pre-charge gas through said purge valve, residual gas is displaced in said first cavity to said inlet valve.

3. The method of sampling a hydrocarbon gas, comprising the steps of:
   a. providing a sample cylinder having a body having a chamber formed therein;
   b. providing a flexible isolation barrier, and utilizing said flexible isolation barrier to selectively divide said chamber in fluid impermeable fashion into first and second cavities;
   c. forming a first passage associated with said first cavity for selectively allowing the passage of a sample fluid therethrough;
   d. forming a second passage associated with said second cavity for selectively allowing the passage of a pre-charge fluid therethrough;
   e. allowing a flow of pre-charge gas through said second passage, so as to urge said flexible isolation barrier toward said first cavity, displacing residual gas in said first cavity;
   f. pressurizing said second cavity via said second passage with a pre-charge gas;
   g. flowing a sample gas through said first passage and into said first cavity;
   h. utilizing said flexible isolation barrier to prevent throttling of said sample gas entering said first cavity; while
   i. providing controlled flow of said sample gas into said sample cylinder by selective venting of said pre-charge gas from said second chamber, until said pre-charge gas is depleted from said second cavity, said flexible isolation barrier conforms to the interior of said chamber, and said sample gas fills said chamber of said sample cylinder.

4. The method of claim 3, wherein in step "e" there is further included the step of allowing said flow of pre-charge gas through said second passage so as to urge said isolation barrier toward said first cavity and to said inlet valve, displacing residual gas in said first cavity to said inlet valve.

5. The method of claim 4, wherein in step "e" there is further included the step of purging any passage upstream of said inlet valve.

6. The method of claim 3, wherein in step "e" said flexible isolation barrier is urged by said pre-charge gas to conform to the interior of said first cavity.

7. The method of sampling a hydrocarbon gas, comprising the steps of:
   a. providing a sample cylinder having a body having a chamber formed therein;
   b. providing a flexible isolation barrier having first and second sides within said chamber;
   c. forming a first passage for selectively allowing the flow of a sample fluid therethrough;
   d. forming a second passage for selectively allowing the flow of a pre-charge fluid therethrough;
   e. initiating a flow of pre-charge gas through said second passage, so as to urge said second side of said flexible isolation barrier to displace residual gas contacting said first side of said flexible isolation barrier within said chamber, while pre-charging said chamber at a pressure;
   g. initiating a flow of sample gas at said pressure through said first passage and into contact with said first side of said flexible isolation barrier;
   h. utilizing said flexible isolation barrier and said pre-charge gas at said pressure contacting said second side of said flexible isolation barrier, to prevent throttling of said sample gas entering said first cavity; while
   i. providing controlled flow of said sample gas into said sample cylinder by selective venting of said pre-charge gas, until said pre-charge gas is depleted from said chamber, said flexible isolation barrier conforms to the interior of said chamber, and said sample gas fills said chamber of said sample cylinder.

8. A sample cylinder, comprising:
   a body having a chamber formed therein, said body having an inlet passage for receiving a sample gas;
   a flexible isolation barrier having first and second sides situated within said chamber;
   said first side of said flexible isolation barrier conformed to contain a sample gas emanating from said inlet passage;
   said second side of said flexible isolation barrier configured to receive pressure from a pre-charge gas situated in said chamber;
   whereby, upon urging said pre-charge gas into said chamber so as to communicate with said second side of said flexible isolation barrier, said second side of said flexible isolation barrier is urged to displace sample gas contained by said flexible isolation barrier, so as to form a pre-charged cylinder; and
   whereby, upon flowing sample gas through said inlet means so as to be contained by said flexible isolation barrier, said sample gas is received in said sample cylinder in controlled fashion by selectively venting said pre-charge gas from said chamber in controlled fashion.

9. The sample cylinder of claim 8, wherein said flexible isolation barrier is formed of polyvinyl fluoride.

10. A sample cylinder, comprising:
   a bowl having a chamber formed therein;
   a head threadingly engaged to said bowl;
   a flexible isolation barrier situated within said chamber, said flexible isolation barrier selectively dividing said chamber into first and second cavities;
   an inlet valve associated with said first cavity; and
   a purge valve associated with said second cavity;
   whereby, upon allowing a flow of pre-charge gas through said purge valve, said isolation barrier is urged toward said first cavity, displacing residual gas in said first cavity; and
   whereby, upon pressurizing said second cavity via said purge valve with a pre-charge gas at a pressure, and flowing a sample gas at said pressure through said inlet valve and into said first cavity, said flexible isolation barrier, receiving pressure from said pre-charge gas from said second cavity, provides controlled flow of said sample gas into said sample cylinder via selective venting of said pre-charge gas from said second chamber, until said pre-charge gas is depleted from said second cavity, and said first chamber is filled with said sample gas.

11. The sample cylinder of claim 10, wherein said inlet valve is formed in said head of said sample cylinder.

12. The sample cylinder of claim 11, wherein there is further provided a passage emanating upstream from said inlet valve.

13. The sample cylinder of claim 12, wherein there is further provided a purge valve associated with said passage upstream from said inlet valve.

14. The sample cylinder of claim 10, wherein said purge valve is formed in said head of said sample cylinder.

15. The sample cylinder of claim 14, wherein said inlet valve is situated adjacent to said first cavity.

16. The sample cylinder of claim 15, wherein said inlet valve is formed in said bowl.

17. The sample cylinder of claim 15, wherein said inlet valve is formed in said head.

18. The sample cylinder of claim 10, wherein said flexible isolation barrier forms a container having a mouth having a periphery, and wherein said mouth engages said head via a retention ring.

19. The method of purging a sample cylinder of residual gas, comprising the steps of:
   a. providing a sample cylinder having a chamber formed therein;
   b. providing a flexible isolation barrier having first and second sides within said chamber;
   c. forming an inlet valve adjacent to said chamber for selectively allowing the passage of a sample fluid therethrough;
   d. forming a second passage for selectively allowing the passage of a pre-charge fluid therethrough;
   e. allowing a flow of pre-charge gas through said second passage, so as to urge said second side of said flexible isolation barrier to displace residual gas contacting said first side of said flexible isolation barrier within said chamber, forming displaced residual gas, urging said displaced residual gas through said inlet valve until said flexible barrier has displaced all residual gas, and said first side of said flexible isolation barrier is situated adjacent to said inlet valve.

20. The method of claim 19, wherein there is further provided the additional step after step "e." of venting a passageway upstream of said inlet valve so as to purge said upstream passageway of contaminants.

21. The method of sampling a fluid, comprising the steps of:
   a. providing a sample cylinder having a chamber formed therein;
   b. providing a flexible isolation barrier having first and second sides within said chamber;
   c. forming an inlet valve adjacent to said chamber for selectively allowing the passage of a sample fluid therethrough;
   d. forming a second passage for selectively allowing the passage of a pre-charge fluid therethrough;
   e. allowing a flow of pre-charge gas through said second passage, so as to urge said second side of said flexible isolation barrier to displace residual gas contacting said first side of said flexible isolation barrier within said chamber, forming displaced residual gas, urging said displaced residual gas through said inlet valve until said flexible barrier has displaced all residual gas, and said first side of said flexible isolation barrier is situated adjacent to said inlet valve, while pre-charging said chamber to a pressure;
   f. flowing a sample gas at said pressure through said inlet valve so as to be contained by said first side of said flexible isolation barrier;
   g. utilizing said flexible isolation barrier, and said pre-charge gas at said pressure contacting said second side of said flexible isolation barrier, to prevent throttling of said sample gas entering said first cavity; while
   i. providing controlled flow of said sample gas into said sample cylinder by selective venting of said pre-charge gas, until said pre-charge gas is depleted from said chamber, said flexible isolation barrier conforms to the interior of said chamber, and said sample gas fills said chamber of said sample cylinder.

22. The method of sampling a hydrocarbon gas, comprising the steps of:
   a. providing a sample cylinder having a bowl having a chamber formed therein and a head removeably engageable to said bowl;
   b. providing a flexible isolation barrier situated in said chamber, and utilizing said flexible isolation barrier to selectively divide said chamber in fluid impermeable fashion into first and second cavities;
   c. pressurizing said second cavity by flowing a precharge gas through a second passage into said second cavity with a pre-charge gas at a pressure;
   d. flowing a sample gas at said pressure through a first passage and into said first cavity;
   e. utilizing said flexible isolation barrier, receiving about equal pressure from said pre-charge gas from said second cavity, to prevent throttling of said sample gas entering said first cavity; while
   f. providing controlled flow of said sample gas into said sample cylinder by selective venting of said pre-charge gas from said second chamber, until said pre-charge gas is depleted from said second cavity, said flexible isolation barrier conforms to the interior of said chamber, and said sample gas fills said chamber of said sample cylinder.

23. The method of claim 22, wherein in step "f" said flexible isolation barrier is urged by said pre-charge gas to conform to the interior of said first cavity.

24. A fluid container, comprising:
 a body having a chamber formed therein;
 a flexible isolation barrier situated within said chamber, said flexible isolation barrier having first and second sides;
 an inlet valve associated with said first side of said flexible isolation barrier; and
 a purge valve associated with said second side of said flexible isolation barrier;
 whereby, upon allowing a flow of pre-charge gas through said purge valve, said isolation barrier displaces fluid situated between said first side of said flexible isolation barrier and said inlet valve; and
 whereby, upon flowing a sample gas through said inlet valve, said first side of said flexible isolation barrier forms a barrier to prevent said sample gas from mixing with said pre-charge gas, while said second side of said flexible isolation barrier and said pre-charge gas regulates the flow of said sample gas into said chamber via selective venting of said pre-charge gas, until said pre-charge gas is depleted from said chamber, said flexible isolation barrier conforms to the interior of said chamber, and said chamber is filled with said sample gas.

25. A method of sampling a gas, comprising the steps of:
 a. providing a fluid container comprising a body having a chamber formed therein;
 b. providing an isolation barrier situated within said chamber, said isolation barrier having first and second sides;
 c. providing an inlet valve associated with said first side of said isolation barrier;
 d. providing a purge valve associated with said second side of said isolation barrier;
 e. flowing a pre-charge gas through said purge valve, so as to urge said isolation barrier to displace fluid situated between said first side of said isolation barrier and said inlet valve;
 f. flowing a sample gas through said inlet valve;
 g. utilizing said isolation barrier to prevent said sample gas from mixing with said pre-charge gas, while utilizing said sample gas to urge said isolation barrier to displace fluid situated between said second side of said isolation barrier and said purge valve; and
 h. providing controlled flow of said sample gas into said fluid container by selective venting of said pre-charge gas, until said pre-charge gas is depleted from said chamber and said sample gas fills said chamber of said fluid container.

* * * * *